(12) United States Patent
Wickersham et al.

(10) Patent No.: US 11,806,323 B2
(45) Date of Patent: *Nov. 7, 2023

(54) TOPICAL ANESTHETICS

(71) Applicant: PTC Innovations, LLC, San Antonio, TX (US)

(72) Inventors: Pendleton Wickersham, San Antonio, TX (US); Stephen Bendel, Las Cruces, NM (US); Todd Mathis, San Antonio, TX (US); Christian Warren, Larkspur, CO (US)

(73) Assignee: PTC Innovations, LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/072,642

(22) Filed: Nov. 30, 2022

(65) Prior Publication Data
US 2023/0285332 A1    Sep. 14, 2023

Related U.S. Application Data

(62) Division of application No. 17/689,827, filed on Mar. 8, 2022, now Pat. No. 11,596,612.
(Continued)

(51) Int. Cl.
*A61K 31/4453* (2006.01)
*A61K 31/495* (2006.01)
(Continued)

(52) U.S. Cl.
CPC ........ *A61K 31/167* (2013.01); *A61K 31/4453* (2013.01); *A61K 31/495* (2013.01);
(Continued)

(58) Field of Classification Search
CPC .............. A61K 31/167; A61K 31/4453; A61K 31/495; A61P 23/02
See application file for complete search history.

(56) References Cited

U.S. PATENT DOCUMENTS

| 4,026,663 A | 5/1977 | Huffman et al. |
| 4,310,429 A | 1/1982 | Lai |

(Continued)

FOREIGN PATENT DOCUMENTS

| AU | 9170939 A | 5/1991 |
| EP | 3666769 A1 | 6/2020 |

(Continued)

OTHER PUBLICATIONS

US 5,889,182 A, 03/1999, Dezube et al. (withdrawn)

(Continued)

*Primary Examiner* — Savitha M Rao
*Assistant Examiner* — Andrew P Lee
(74) *Attorney, Agent, or Firm* — Incubate IP; Randy R. Micheletti

(57) ABSTRACT

The present disclosure provides compounds useful as anesthetics, such as topical anesthetics, of general formula (VI):

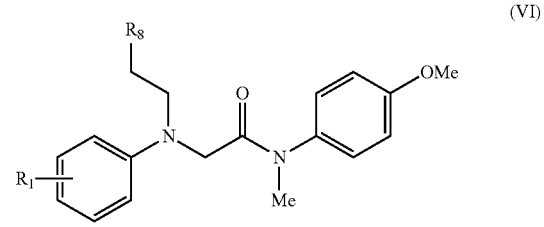

wherein:
$R_1$ is H, Cl, F, —$CF_3$, —$OCF_3$, —OMe, or methyl;
$R_8$ is selected from the group consisting of:
—$NH_2$, —N(H)Alk, —N(Alk)$_2$, (Continued)

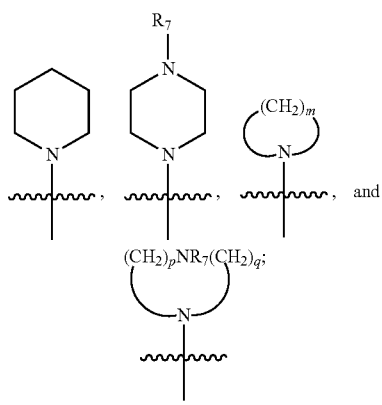

$R_7$ is H or alkyl;
m is 3 to 6;
p is 1 to 4;
q is 1 to 4;
p+g is 3 to 6; and
each Alk is independently an aliphatic carbon group consisting of 1 to 6 carbon atoms,
and methods of making and using same.

20 Claims, 7 Drawing Sheets

Related U.S. Application Data

(60) Provisional application No. 63/317,868, filed on Mar. 8, 2022.

(51) Int. Cl.
  *A61P 23/02* (2006.01)
  *A61K 31/167* (2006.01)
  *A61K 45/06* (2006.01)
  *C07C 233/29* (2006.01)

(52) U.S. Cl.
  CPC .............. *A61K 45/06* (2013.01); *A61P 23/02* (2018.01); *C07C 233/29* (2013.01)

(56) References Cited

U.S. PATENT DOCUMENTS

| | | |
|---|---|---|
| 4,489,186 A | 12/1984 | Sugio et al. |
| 5,244,898 A | 9/1993 | Ogawa et al. |
| 5,258,510 A | 11/1993 | Ogawa et al. |
| 5,336,800 A | 8/1994 | Siegel et al. |
| 5,382,590 A | 1/1995 | Bourzat et al. |
| 5,389,682 A | 2/1995 | Tait et al. |
| 5,447,916 A | 9/1995 | Spellmeyer et al. |
| 5,475,106 A | 12/1995 | Bourzat et al. |
| 5,480,871 A | 1/1996 | Spellmeyer et al. |
| 5,494,926 A | 2/1996 | Owens et al. |
| 5,559,230 A | 9/1996 | Ogawa et al. |
| 5,753,677 A | 5/1998 | Ogawa et al. |
| 5,830,854 A | 11/1998 | Hargreaves |
| 5,985,869 A | 11/1999 | Ogawa et al. |
| 6,103,761 A | 8/2000 | Tait et al. |
| 6,159,482 A | 12/2000 | Tuloup et al. |
| 6,326,014 B1 | 12/2001 | Tuloup et al. |
| 6,350,761 B1 | 2/2002 | Guilford et al. |
| 6,420,396 B1 | 7/2002 | Albers et al. |
| 6,610,749 B2 | 8/2003 | Liao et al. |
| 6,677,333 B1 | 1/2004 | Seko et al. |
| 6,677,360 B2 | 1/2004 | Albers et al. |
| 6,743,788 B2 | 6/2004 | Cirillo et al. |
| 7,049,911 B2 | 8/2006 | Albers et al. |
| 7,172,631 B2 | 2/2007 | Plos et al. |
| 7,189,266 B2 | 3/2007 | Plos et al. |
| 7,261,743 B2 | 8/2007 | Plos et al. |
| 7,265,133 B2 | 9/2007 | Mammen et al. |
| 7,456,199 B2 | 11/2008 | Mammen et al. |
| 7,491,718 B2 | 2/2009 | Comess et al. |
| 7,642,355 B2 | 1/2010 | Mu et al. |
| 7,795,315 B2 | 9/2010 | Chen et al. |
| 7,851,632 B2 | 12/2010 | Mammen et al. |
| 7,858,795 B2 | 12/2010 | Mammen et al. |
| 8,303,487 B2 | 11/2012 | Ueno et al. |
| 8,329,911 B2 | 12/2012 | Mu et al. |
| 8,394,965 B2 | 3/2013 | Mauduit et al. |
| 8,466,161 B2 | 6/2013 | Lee et al. |
| 8,586,757 B2 | 11/2013 | Mauduit et al. |
| 8,853,240 B2 | 10/2014 | Menet et al. |
| 9,198,420 B2 | 12/2015 | Hopkins et al. |
| 9,415,037 B2 | 8/2016 | Menet et al. |
| 9,505,754 B2 | 11/2016 | Menet et al. |
| 2004/0068012 A1 | 4/2004 | Comess et al. |
| 2004/0087582 A1 | 5/2004 | Dorsch et al. |
| 2004/0157836 A1 | 8/2004 | Comess et al. |
| 2005/0113426 A1 | 5/2005 | Liao et al. |
| 2006/0139425 A1 | 6/2006 | Tsuchimura et al. |
| 2007/0098816 A1 | 5/2007 | Nakanishi et al. |
| 2008/0221127 A1 | 9/2008 | Lin et al. |
| 2009/0000558 A1 | 1/2009 | Matsuo et al. |
| 2009/0264412 A1 | 10/2009 | Kampen et al. |
| 2010/0093998 A1 | 4/2010 | Isobe et al. |
| 2011/0028715 A1 | 2/2011 | Isobe et al. |

FOREIGN PATENT DOCUMENTS

| | | |
|---|---|---|
| JP | 11180964 A | 7/1999 |
| JP | 11269146 A | 10/1999 |
| WO | 97/29121 A1 | 8/1997 |
| WO | 97/45115 A1 | 12/1997 |
| WO | 2000/035864 A1 | 6/2000 |
| WO | 2017/213137 A1 | 12/2017 |
| WO | 2022/026548 A1 | 2/2022 |

OTHER PUBLICATIONS

Alles, et al., "Etiology and Pharmacology of Neuropathic Pain," *Pharmacol. Rev.*, vol. 70, pp. 315-347 (Apr. 2018).
Danziger, et al., "Automated site-directed drug design: a general algorithm for knowledge acquisition about hydrogen-bonding regions a protein surfaces," *Proc. R. Soc. Lond. B*, vol. 236, pp. 101-113 (1989).
Hirst et al., "Conversion of acyclic nonpeptide CCK antagonists into CCK agonists," *Bioorg. & Med. Chem. Lett.*, vol. 7(5), pp. 511-514 (1997).
PCT Int'l Search Report and Written Opinion for corresponding PCT/US23/14782 (dated Jul. 27, 2023), 12 pages.
Jain et al., "Recent Advances in Lipid-Based Vesicles and Particulate Carriers for Topical and Transdermal Application," *J. Pharm. Sci.*, vol. 106, pp. 423-445 (2017), 23 pages.
Naccache et al., "Patterns of Nonelectrolyte Permeability in Human Red Blood Cell Membrane," *J. Gen. Phys.*, vol. 62, pp. 714-736 (1973), 23 pages.
Pubchem, "Substance Record: AKOS009151473," SID 145462736, version 3, available at https://pubchem.ncbi.nlm.nih.gov/substance/145462736 (last modified Jun. 2, 2019), 7 pages.

TOPICAL ANESTHETICS

PRIORITY CLAIM

This application is a divisional application of U.S. patent application Ser. No. 17/689,827, filed on Mar. 8, 2022, which claims priority to U.S. Provisional Patent Application Ser. No. 63/317,868, filed Mar. 8, 2022, the entire contents of each of which are incorporated herein by reference and relied upon.

FIELD

The present disclosure provides compounds useful as anesthetic agents methods of making same, compositions comprising same, and methods of treating or preventing pain using same.

BACKGROUND

Anesthetic agents are commonly used to treat or prevent pain sensations. However, certain classes of anesthetics encourage overuse, abuse, and/or overprescribing. Other agents are potent, but provide low bioavailability for example when administered topically.

A need persists for improved anesthetic agents, especially agents that are effective when applied topically to skin of a subject.

SUMMARY

In one embodiment, the present disclosure provides a compound of formula (I):

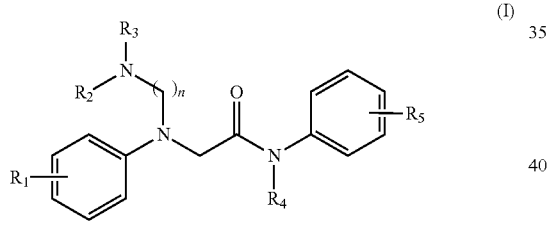

(I)

wherein:
$R_1$ is H, —OMe, Me, or one or more electron withdrawing groups;
$R_2$ and $R_3$ are each independently H or alkyl or, taken together, form a 4- to 8-membered heterocyclic ring with the adjacent nitrogen atom;
$R_4$ is H or alkyl;
$R_5$ is H or one or more electron donating groups; and
n is 1 to 4.

In other embodiments, the present disclosure provides a compound of formula (II):

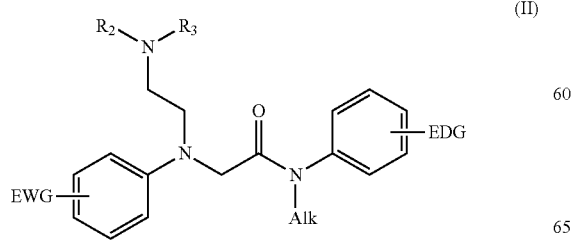

(II)

wherein:
EWG is one or more electron withdrawing groups selected from the group consisting of: Cl, F, $CF_3$, and $OCF_3$;
$R_2$ and $R_3$ are each independently H or alkyl; Alk is an aliphatic carbon group consisting of 1 to 6 carbon atoms; and
EDG is one or more alkoxy or alkyl electron donating groups.

In other embodiments, the present disclosure provides a compound of formula (III):

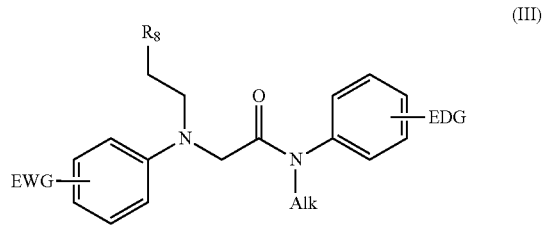

(III)

wherein:
EWG is one or more electron withdrawing groups selected from the group consisting of: Cl, F, $CF_3$, and $OCF_3$;
$R_8$ is selected from the group consisting of:
—$NH_2$, —N(H)Alk, —N(Alk)$_2$,

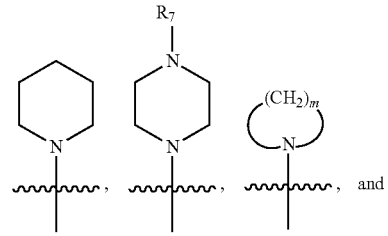, and

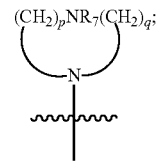;

$R_7$ is H or alkyl;
m is 3 to 6;
p is 1 to 4;
q is 1 to 4;
p+q is 3 to 6;
each Alk is independently an aliphatic carbon group consisting of 1 to 6 carbon atoms; and
EDG is one or more alkoxy or alkyl electron donating groups.

In other embodiments, the present disclosure provides a compound of formula (IV):

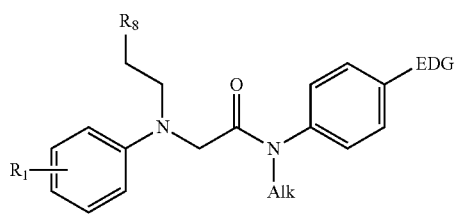

(IV)

wherein:

R₁ is H, Cl, F, —CF₃, —OCF₃, or —OMe;

R₈ is selected from the group consisting of:
—NH₂, —N(H)Alk, —N(Alk)₂,

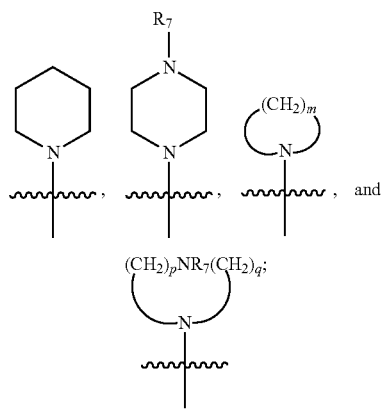

R₇ is H or alkyl;

m is 3 to 6;

p is 1 to 4;

q is 1 to 4;

p+g is 3 to 6;

each Alk is independently an aliphatic carbon group consisting of 1 to 6 carbon atoms; and EDG is one or more amino, aryl, acylamido, acyloxy, alkoxy or alkyl electron donating groups.

In other embodiments, the present disclosure provides a compound of formula (V):

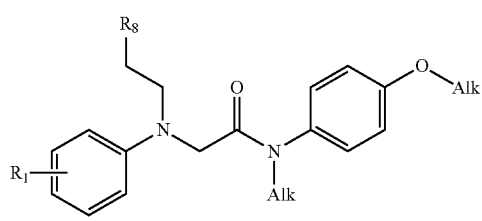

(V)

wherein:

R₁ is H, Cl, F, —CF₃, —OCF₃, or —OMe;

R₈ is selected from the group consisting of:
—NH₂, —N(H)Alk, —N(Alk)₂,

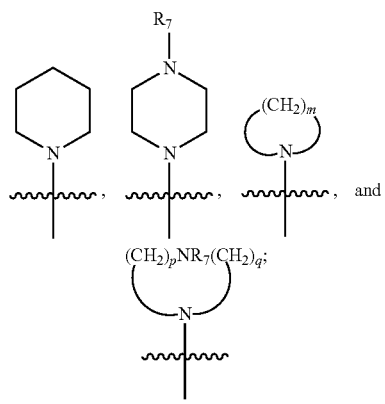

R₇ is H or alkyl;

m is 3 to 6;

p is 1 to 4;

q is 1 to 4;

p+g is 3 to 6; and each Alk is independently an aliphatic carbon group consisting of 1 to 6 carbon atoms.

In other embodiments, the present disclosure provides a compound of formula (VI):

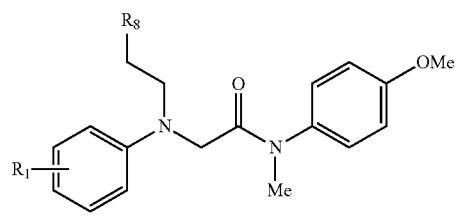

(VI)

wherein:

R₁ is H, Cl, F, —CF₃, —OCF₃, —OMe, or methyl;

R₈ is selected from the group consisting of:
—NH₂, —N(H)Alk, —N(Alk)₂,

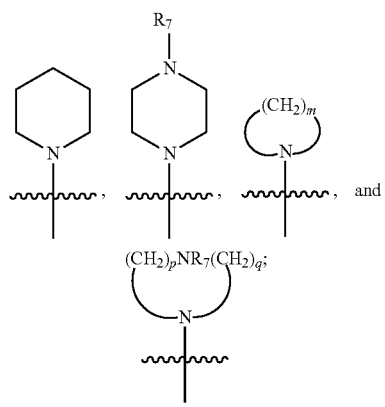

R₇ is H or alkyl;

m is 3 to 6;

p is 1 to 4;

q is 1 to 4;

p+g is 3 to 6; and each Alk is independently an aliphatic carbon group consisting of 1 to 6 carbon atoms.

In other embodiments, the present disclosure provides a compound of formula (VII):

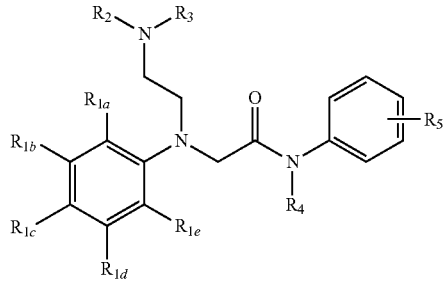

(VII)

wherein:
R$_{1a}$ is H, Cl, F, —CF$_3$, —OMe, or methyl;
R$_{1b}$ is H, Cl, F, —CF$_3$, or —OCF$_3$;
R$_{1c}$ is H, Cl, F, or —OMe;
R$_{1d}$ is H, Cl, F, —CF$_3$, or —OCF$_3$;
R$_{1e}$ is H, Cl, F, —CF$_3$, —OMe, or methyl;
R$_2$ and R$_3$ are each independently H or alkyl or, taken together, form a 4- to 8-membered heterocyclic ring with the adjacent nitrogen atom;
R$_4$ is H or alkyl; and
R$_5$ is H or one or more electron donating groups.

In other embodiments, the present disclosure provides a composition comprising a compound of any one of formulas (I) to (VII).

In other embodiments, the present disclosure provides a method of treating or preventing pain in a subject, the method comprising topically applying the composition comprising a compound of any one of formulas (I) to (VII) to skin of the subject proximal to perceived pain or expected pain.

DETAILED DESCRIPTION

Figure 1:
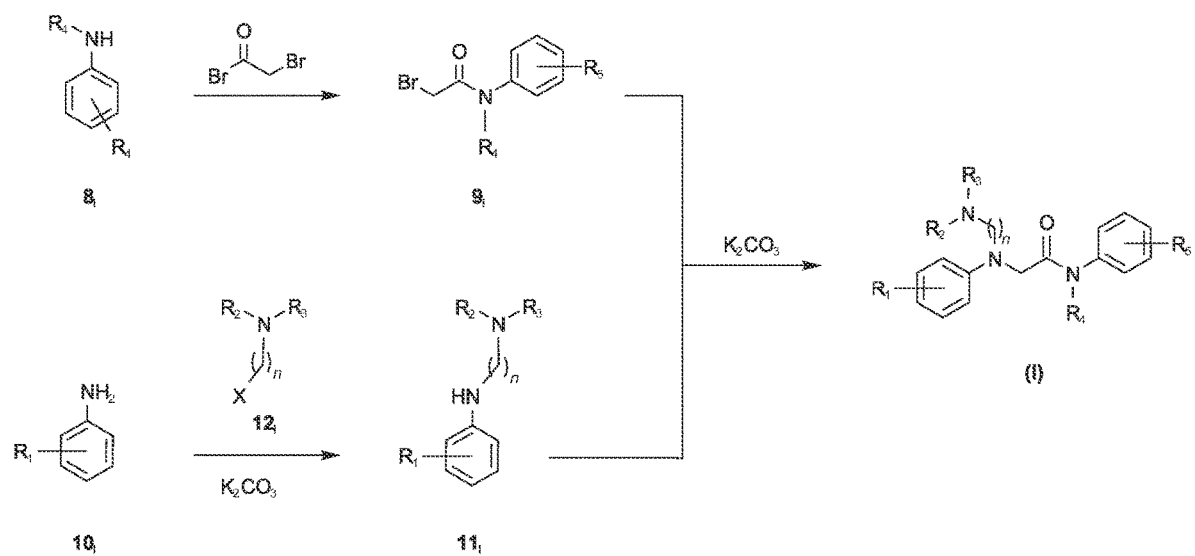
FIG. 1 shows a representative synthetic route for producing compounds of formula (I).

The present disclosure provides compounds useful as anesthetic agents, for example to treat or prevent pain when applied topically to skin of a subject, and methods of making such compounds and using such compounds to treat or prevent pain.

1. Anesthetic Compounds

The present disclosure provides compounds of formula (I):

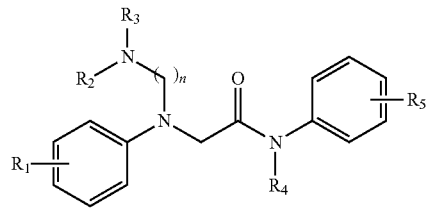

(I)

wherein:
R$_1$ is H, alkyl, alkoxy, or one or more electron withdrawing groups;
R$_2$ and R$_3$ are each independently H or alkyl or, taken together, form a 4- to 8-membered heterocyclic ring with the adjacent nitrogen atom;
R$_4$ is H or alkyl;
R$_5$ is H or one or more electron donating groups; and
n is 1 to 4.

The present disclosure also provides salts of compounds of formula (I), which may be prepared for example by contacting a neutral compound of formula (I) with an acid (e.g., hydrochloric acid) to form a salt (e.g., a hydrochloride salt) of the compound of formula (I). A suitable salt of a compound of formula (I) is a salt of a mineral or organic acid. Suitable mineral acids include hydrochloric, hydrobromic, hydroiodic, nitric or sulfuric acid. A suitable organic acid is, for example, an organic achiral acid such as acetic, trifluoroacetic, oxalic or p-toluenesulfonic acid, or an organic chiral acid such as L-tartaric acid, dibenzoyl-L-tartaric acid or di-p-toluoyl-L-tartaric acid.

The present disclosure also provides hydrates of compounds of formula (I).

In some embodiments, R$_1$ is selected from the group consisting of: H, alkyl, alkoxy, and electron withdrawing groups. In some embodiments, only one R$_1$ group is present and may be at the ortho-, meta-, or para-position of the aryl ring. In other embodiments, two to five R$_1$ groups are present, and each R$_1$ group is independently selected from the group consisting of H, alkyl, alkoxy, and electron withdrawing groups, and each R$_1$ group located at any combination of the ortho-, meta-, and para-positions of the aryl ring. For example and without limitation, two R$_1$ groups may be present in a compound of formula (I) consistent with the present disclosure, and each R$_1$ group is independently selected from the group consisting of H, alkyl, alkoxy, and electron withdrawing groups. In other embodiments, three R$_1$ groups are present, and each R$_1$ group is independently selected from the group consisting of H, alkyl, alkoxy, and electron withdrawing groups. In still other embodiments, four R$_1$ groups are present. In other embodiments, five R$_1$ groups are present, and each R$_1$ group is independently selected from the group consisting of H, alkyl, alkoxy, and electron withdrawing groups.

When R$_1$ is alkyl, the alkyl group may be linear or branched, and may consist of one to six carbon atoms (i.e., C$_{1-6}$ alkyl). The alkyl group may be cyclic, in which case the alkyl group may consist of three to six carbon atoms (i.e., C$_{3-6}$ cycloalkyl). The alkyl group may be saturated or unsaturated with one or more carbon-carbon double bonds and/or carbon-carbon triple bonds.

When R$_1$ is alkoxy, the alkoxy group may be linear or branched, and may consist of one to six carbon atoms (i.e., C$_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds.

When $R_1$ is an electron withdrawing group, the electron withdrawing group may be a halogen, a halogenated alkyl group, or a halogenated alkoxy group. For example and without limitation, the electron withdrawing group may be a halogen, a halogen-substituted alkyl, a halogen-substituted alkoxyl, a perhaloalkyl, or a perhaloalkoxy. fluoro, In some embodiments, each electron withdrawing group is independently selected from chloro, bromide, iodide, halomethyl, dihalomethyl, trihalomethyl, halomethoxyl, dihalomethoxyl, and trihalomethoxyl. In some embodiments, each electron withdrawing group is independently selected from the group consisting of fluoro, chloro, trifluoromethyl, and trifluoromethoxyl.

Each $R_2$ and $R_3$ are each independently H or alkyl or, taken together, form a 4- to 8-membered heterocyclic ring with the adjacent nitrogen atom. In some embodiments, $R_2$ is H while $R_3$ is alkyl. In some embodiments, both $R_2$ and $R_3$ are alkyl. When $R_2$ and/or $R_3$ are alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

In some embodiments, $R_2$ and $R_3$ are covalently connected to form, with the adjacent nitrogen atom, a heterocyclic ring. The heterocyclic ring may include one to three nitrogen atoms and a total of four to eight atoms in the ring. The heterocyclic ring may be unsubstituted or substituted, for example with an alkyl or alkoxyl group. For example and without limitation, $R_2$ and $R_3$ may be covalently connected and include a total of five carbon atoms to form a piperidinyl ring including the nitrogen atom adjacent to $R_2$ and $R_3$. In other embodiments, $R_2$ and $R_3$ may, together, have a general formula —$(CH_2)_pN(R_7)(CH_2)_q$—, wherein p is 1 to 4, q is 1 to 4, p and q combined total 3 to 8, and $R_7$ is H or alkyl. When $R_7$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloal-kyl). The alkyl group may be saturated or unsaturated with one or more carbon-carbon double bonds and/or carbon-carbon triple bonds.

$R_4$ is H or alkyl. When $R_4$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

$R_5$ is H or one or more electron donating groups. When $R_5$ is one or more electron donating groups, $R_5$ may be a single electron donating group in the ortho-, meta-, or para-position of the aryl ring. In other embodiments, $R_5$ may be two to five electron donating groups in any combination of ortho-, meta-, and para-positions of the aryl ring. Each electron donating group may be independently selected from alkyl and alkoxyl. When $R_5$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When $R_5$ is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds.

The number of methylene groups (n) in compounds of formula (I) may be 1 to 4. In some embodiments, n is 1. In other embodiments, n is 2. In other embodiments, n is 3. In other embodiments, n is 4.

Some example compounds of formula (I) are provided in Table 1 below.

TABLE 1

Example Compounds of Formula (I)

| Compound | $R_1$ | $R_2$ | $R_3$ | $R_4$ | $R_5$ | $R_7$ | n | p | q |
|---|---|---|---|---|---|---|---|---|---|
| 2290 | H | Me | Me | Me | p-OMe | n/a | 2 | n/a | n/a |
| 2291 | m-Cl | Me | Me | Me | p-OMe | n/a | 2 | n/a | n/a |
| 2292 | m-Cl p-Cl | Me | Me | Me | p-OMe | n/a | 2 | n/a | n/a |
| 2293 | o-OMe | Me | Me | Me | p-OMe | n/a | 2 | n/a | n/a |
| 2294 | p-OMe | Me | Me | Me | p-OMe | n/a | 2 | n/a | n/a |
| 2295 | o-Me | Me | Me | Me | p-OMe | n/a | 2 | n/a | n/a |
| 2296 | m-OCF$_3$ | Me | Me | Me | p-OMe | n/a | 2 | n/a | n/a |
| 2297 | m-CF$_3$ p-Cl | Me | Me | Me | p-OMe | n/a | 2 | n/a | n/a |
| 2298 | 2-Cl 5-Cl | Me | Me | Me | p-OMe | n/a | 2 | n/a | n/a |
| 2299 | m-Cl p-F | Me | Me | Me | p-OMe | n/a | 2 | n/a | n/a |
| 2300 | 2-F 3-Cl | Me | Me | Me | p-OMe | n/a | 2 | n/a | n/a |
| 2301 | o-CF$_3$ | Me | Me | Me | p-OMe | n/a | 2 | n/a | n/a |
| 2302 | H | H | H | Me | p-OMe | n/a | 2 | n/a | n/a |
| 2303 | H | —(CH$_2$)$_5$— | | Me | p-OMe | n/a | 2 | n/a | n/a |
| 2304 | H | —(CH$_2$)$_p$N(R$_7$)(CH$_2$)$_q$— | | Me | p-OMe | Me | 2 | 2 | 2 |

Referring now to FIG. 1, compounds consistent with formula (I) can be synthesized by, for example, acylating anilines $8_I$ with bromoacetyl bromide to form α-bromoamido intermediates $9_I$. Intermediates $11_I$ can be formed by alkylating anilines $10_I$ with β-haloamines $12_I$ in the presence of base. Combining intermediates $11_I$ with the α-bromoamido intermediates 9$_I$ in the presence of base yields compounds of formula (I).

The present disclosure also provides compounds of formula (II):

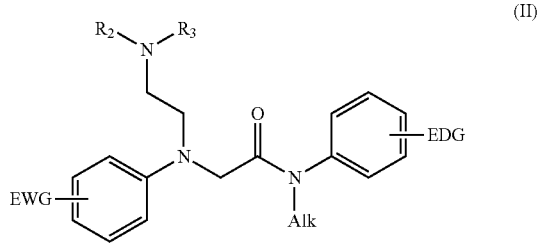

(II)

wherein:
- EWG is one or more electron withdrawing groups selected from the group consisting of: Cl, F, halogenated alkyl, and halogenated alkoxyl;
- $R_2$ and $R_3$ are each independently H or alkyl;
- Alk is an aliphatic carbon group consisting of 1 to 6 carbon atoms; and
- EDG is one or more alkoxy or alkyl electron donating groups.

In compounds of formula (II), EWG is one or more electron withdrawing groups each independently selected from the group consisting of: Cl, F, halogenated alkyl, and halogenated alkoxyl. For example and without limitation, EWG may in some embodiments be a single electron withdrawing group located at the ortho-, meta-, or para-position of the aryl ring. In other embodiments, EWG is two or more electron withdrawing groups located at any combination of the ortho-positions, the meta-positions, and the para-position of the aryl ring.

Each EWG may independently be selected from the group consisting of chloro, fluoro, halogenated alkyl, and halogenated alkoxyl. The halogenated alkyl may be monohaloalkyl, dihaloalkyl, trihaloalkyl, or perhaloalkyl and may have 1 to 6 carbon atoms (i.e., $C_{1-6}$ haloalkyl). The haloalkyl electron withdrawing group may be saturated or unsaturated. The halogenated alkyl may be branched, linear, or cyclic. In some embodiments, the electron withdrawing group is trifluoromethyl. The halogenated alkoxyl may be monohaloalkoxyl, dihaloalkoxyl, trihaloalkoxyl, or perhaloalkoxyl and may have 1 to 6 carbon atoms (i.e., $C_{1-6}$ haloalkoxyl). The haloalkoxyl electron withdrawing group may be saturated or unsaturated. The halogenated alkoxyl may be branched, linear, or cyclic. In some embodiments, the electron withdrawing group is trifluoromethoxyl.

Each $R_2$ and $R_3$ is independently H or alkyl. When $R_2$ and/or $R_3$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

EDG is one or more alkoxy or alkyl electron donating groups. EDG may be a single electron donating group in the ortho-, meta-, or para-position of the aryl ring. In other embodiments, EDG may be two to five electron donating groups in any combination of ortho-, meta-, and para-positions of the aryl ring. Each EDG may be independently selected from alkyl and alkoxyl. When EDG is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds. In some embodiments, EDG is para-alkoxy, such as para-methoxy, para-ethoxy, or para-propoxy.

Some example compounds of formula (II) are provided in Table 2 below.

TABLE 2

Example Compounds of Formula (II)

| Compound | EWG | $R_2$ | $R_3$ | Alk | EDG | $R_7$ | n | p | q |
|---|---|---|---|---|---|---|---|---|---|
| 2290 | H | Me | Me | Me | p-OMe | n/a | 2 | n/a | n/a |
| 2291 | m-Cl | Me | Me | Me | p-OMe | n/a | 2 | n/a | n/a |
| 2292 | m-Cl p-Cl | Me | Me | Me | p-OMe | n/a | 2 | n/a | n/a |
| 2293 | o-OMe | Me | Me | Me | p-OMe | n/a | 2 | n/a | n/a |
| 2294 | p-OMe | Me | Me | Me | p-OMe | n/a | 2 | n/a | n/a |
| 2295 | o-Me | Me | Me | Me | p-OMe | n/a | 2 | n/a | n/a |
| 2296 | m-OCF$_3$ | Me | Me | Me | p-OMe | n/a | 2 | n/a | n/a |
| 2297 | m-CF$_3$ p-Cl | Me | Me | Me | p-OMe | n/a | 2 | n/a | n/a |
| 2298 | 2-Cl 5-Cl | Me | Me | Me | p-OMe | n/a | 2 | n/a | n/a |
| 2299 | m-Cl p-F | Me | Me | Me | p-OMe | n/a | 2 | n/a | n/a |
| 2300 | 2-F 3-Cl | Me | Me | Me | p-OMe | n/a | 2 | n/a | n/a |
| 2301 | o-CF$_3$ | Me | Me | Me | p-OMe | n/a | 2 | n/a | n/a |
| 2302 | H | H | H | Me | p-OMe | n/a | 2 | n/a | n/a |

TABLE 2-continued

Example Compounds of Formula (II)

| Compound | EWG | R$_2$ | R$_3$ | Alk | EDG | R$_7$ | n | p | q |
|---|---|---|---|---|---|---|---|---|---|
| 2303 | H | —(CH$_2$)$_5$— | | Me | p-OMe | n/a | 2 | n/a | n/a |
| 2304 | H | —(CH$_2$)$_p$N(R$_7$)(CH$_2$)$_q$— | | Me | p-OMe | Me | 2 | 2 | 2 |

Figure 2:
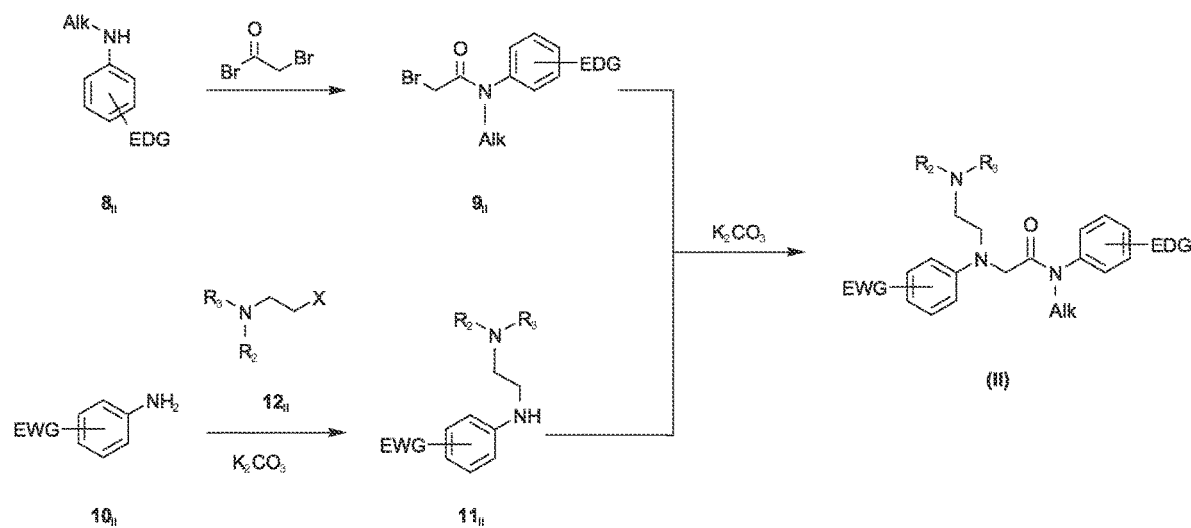
FIG. 2 shows a representative synthetic route for producing compounds of formula (II).

Referring now to FIG. 2, compounds consistent with formula (II) can be synthesized by, for example, acylating alkylanilines $8_{II}$ with bromoacetyl bromide to form α-bromoamido intermediates $9_{II}$. Intermediates $11_{II}$ can be formed by alkylating anilines $10_{II}$ with β-haloamines $12_{II}$ in the presence of base. Combining intermediates $11_{II}$ with the α-bromoamido intermediates $9_{II}$ in the presence of base yields compounds of formula (II).

The present disclosure also provides compounds of formula (III):

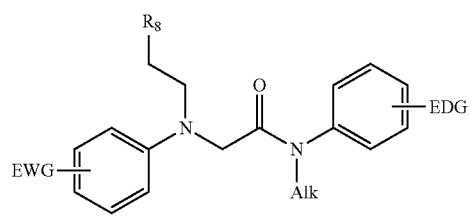

(III)

wherein:
EWG is one or more electron withdrawing groups selected from the group consisting of: Cl, F, CF$_3$, and OCF$_3$;
R$_8$ is selected from the group consisting of:
—NH$_2$, —N(H)Alk, —N(Alk)$_2$,

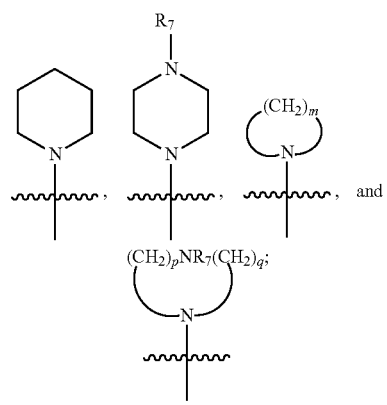

R$_7$ is H or alkyl;
m is 3 to 6;
p is 1 to 4;
q is 1 to 4;
p+q is 3 to 6;
each Alk is independently an aliphatic carbon group consisting of 1 to 6 carbon atoms; and
EDG is one or more alkoxy or alkyl electron donating groups.

In compounds of formula (III), EWG is one or more electron withdrawing groups each independently selected from the group consisting of: chloro, fluoro, trifluoromethyl, and trifluoromethoxy. For example and without limitation, EWG may in some embodiments be a single electron withdrawing group that is chloro, fluoro, trifluoromethyl, or trifluoromethoxy that is located at the ortho-, meta-, or para-position of the aryl ring. In other embodiments, EWG is two or more electron withdrawing groups independently selected from chloro, fluoro, trifluoromethyl, and trifluoromethoxy located at any combination of the ortho-positions, the meta-positions, and the para-position of the aryl ring.

R$_8$ is an n-amino substituent selected from —NH$_2$, —N(H)Alk, —N(Alk)$_2$,

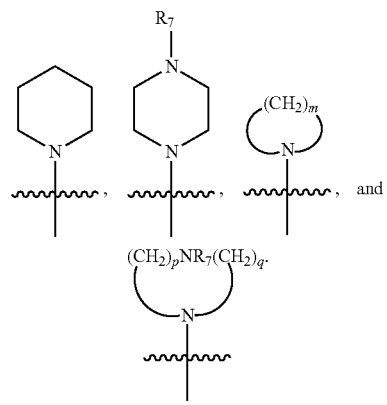

When R$_8$ is —N(H)Alk or —N(Alk)$_2$, Alk is an aliphatic carbon group consisting of 1 to 6 carbon atoms (i.e., C$_{1-6}$ alkyl). Alk may be linear, branched, or cyclic. When Alk is cyclic, the alkyl group may consist of three to six carbon atoms (i.e., C$_{3-6}$ cycloalkyl). The alkyl group may be saturated or unsaturated with one or more carbon-carbon double bonds and/or carbon-carbon triple bonds.

When R$_8$ is

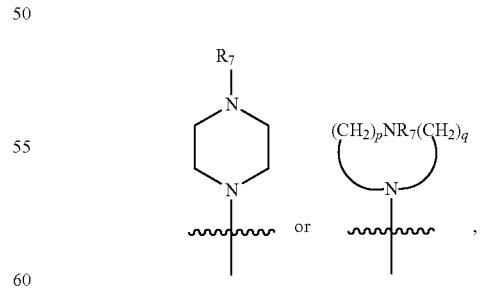

R$_7$ is H or alkyl. When R$_7$ is alkyl, the alkyl group can be an aliphatic carbon group consisting of 1 to 6 carbon atoms (i.e., C$_{1-6}$ alkyl). The alkyl group may be linear, branched, or cyclic. When the alkyl group is cyclic, the alkyl group may consist of three to six carbon atoms (i.e., C$_{3-6}$ cycloalkyl). The alkyl group may be saturated or unsaturated with one or more carbon-carbon double bonds and/or carbon-carbon triple bonds. In some embodiments, $R_7$ is H. In other embodiments, $R_7$ is methyl. In other embodiments, $R_7$ is ethyl. In other embodiments, $R_7$ is propyl (e.g., n-propyl or isopropyl). In other embodiments, $R_7$ is butyl (e.g., 1-butyl, 2-butyl, or t-butyl). In other embodiments, $R_7$ is pentyl (e.g., 1-n-pentyl, 2-n-pentyl, 3-n-pentyl, 2-methylbut-4-yl, 2-methylbutyl-3-yl, or 1-dimethylprop-1-yl). In other embodiments, $R_7$ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethylbut-4-yl, 2,2-dimethylbut-4-yl, 3,3-dimethylbut-4-yl, 2,3,3-trimethylbut-4-yl, 2,2-dimethylbut-4-yl, 1,1-dimethylbut-1-yl, or 1,2,2-trimethylbut-1-yl).

When $R_8$ is

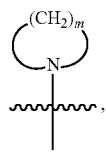

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

When $R_8$ is

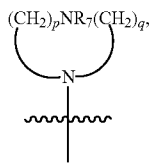

p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3.

EDG is one or more alkoxy or alkyl electron donating groups. EDG may be a single electron donating group in the ortho-, meta-, or para-position of the aryl ring. In other embodiments, EDG may be two to five electron donating groups in any combination of ortho-, meta-, and para-positions of the aryl ring. Each EDG may be independently selected from alkyl and alkoxyl. When EDG is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds. In some embodiments, EDG is para-alkoxy, such as para-methoxy, para-ethoxy, or para-propoxy.

Some example compounds of formula (III) are provided in Table 3 below.

TABLE 3

Example Compounds of Formula (III)

| Compound | EWG | $R_8$ | Alk | EDG | $R_7$ | m | n | p | q |
|---|---|---|---|---|---|---|---|---|---|
| 2290 | H | —N(Alk)$_2$ | Me | p-OMe | n/a | n/a | 2 | n/a | n/a |
| 2291 | m-Cl | —N(Alk)$_2$ | Me | p-OMe | n/a | n/a | 2 | n/a | n/a |
| 2292 | m-Cl p-Cl | —N(Alk)$_2$ | Me | p-OMe | n/a | n/a | 2 | n/a | n/a |
| 2293 | o-OMe | —N(Alk)$_2$ | Me | p-OMe | n/a | n/a | 2 | n/a | n/a |
| 2294 | p-OMe | —N(Alk)$_2$ | Me | p-OMe | n/a | n/a | 2 | n/a | n/a |
| 2295 | o-Me | —N(Alk)$_2$ | Me | p-OMe | n/a | n/a | 2 | n/a | n/a |
| 2296 | m-OCF$_3$ | —N(Alk)$_2$ | Me | p-OMe | n/a | n/a | 2 | n/a | n/a |
| 2297 | m-CF$_3$ p-Cl | —N(Alk)$_2$ | Me | p-OMe | n/a | n/a | 2 | n/a | n/a |
| 2298 | 2-Cl 5-Cl | —N(Alk)$_2$ | Me | p-OMe | n/a | n/a | 2 | n/a | n/a |
| 2299 | m-Cl p-F | —N(Alk)$_2$ | Me | p-OMe | n/a | n/a | 2 | n/a | n/a |
| 2300 | 2-F 3-Cl | —N(Alk)$_2$ | Me | p-OMe | n/a | n/a | 2 | n/a | n/a |
| 2301 | o-CF$_3$ | —N(Alk)$_2$ | Me | p-OMe | n/a | n/a | 2 | n/a | n/a |
| 2302 | H | —NH$_2$ | Me | p-OMe | n/a | n/a | 2 | n/a | n/a |
| 2303 | H | 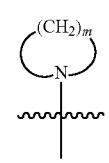 | Me | p-OMe | n/a | 5 | 2 | n/a | n/a |
| 2304 | H | 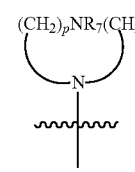 | Me | p-OMe | Me | n/a | 2 | 2 | 2 |

Figure 3:
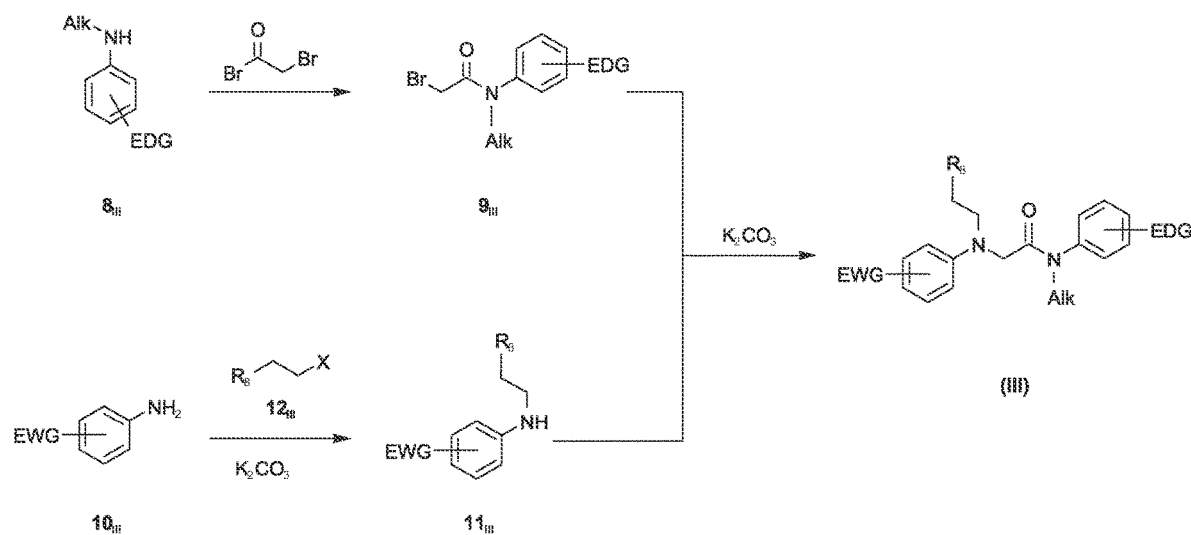
FIG. 3 shows a representative synthetic route for producing compounds of formula (II).

Referring now to FIG. 3, compounds consistent with formula (III) can be synthesized by, for example, acylating alkylanilines $8_{III}$ with bromoacetyl bromide to form α-bromoamido intermediates $9_{III}$. Intermediates $11_{III}$ can be formed by alkylating anilines $10_{III}$ with β-haloamines $12_{III}$ in the presence of base. Combining intermediates $11_{III}$ with the α-bromoamido intermediates $9_{III}$ in the presence of base yields compounds of formula (III).

The present disclosure further provides compounds of formula (IV):

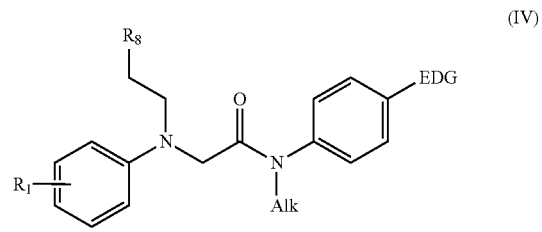

(IV)

wherein:

$R_1$ is H, Cl, F, —CF$_3$, —OCF$_3$, or —OMe;

$R_8$ is selected from the group consisting of:

—NH$_2$, —N(H)Alk, —N(Alk)$_2$,

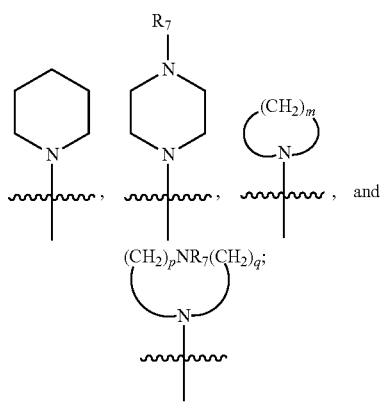

R$_7$ is H or alkyl;
m is 3 to 6;
p is 1 to 4;
q is 1 to 4;
p+q is 3 to 6;
each Alk is independently an aliphatic carbon group consisting of 1 to 6 carbon atoms; and
EDG is one or more amino, aryl, acylamido, acyloxy, alkoxy or alkyl electron donating groups.

In compounds of formula (IV), R$_1$ is H or one or more substituents each independently selected from the group consisting of: chloro, fluoro, trifluoromethyl, trifluoromethoxy, and methoxy. For example and without limitation, R$_1$ may in some embodiments be a single substituent that is chloro, fluoro, trifluoromethyl, trifluoromethoxy, or methoxy that is located at the ortho-, meta-, or para-position of the aryl ring. In other embodiments, R$_1$ is two or more substituents each independently selected from chloro, fluoro, trifluoromethyl, trifluoromethoxy, and methoxy located at any combination of the ortho-positions, the meta-positions, and the para-position of the aryl ring.

R$_8$ is an n-amino substituent selected from —NH$_2$, —N(H)Alk, —N(Alk)$_2$,

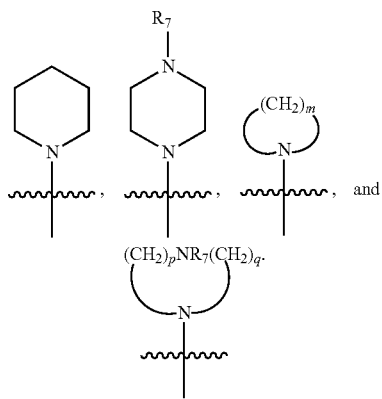

When R$_8$ is —N(H)Alk or —N(Alk)$_2$, Alk is an aliphatic carbon group consisting of 1 to 6 carbon atoms (i.e., C$_{1-6}$ alkyl). Alk may be linear, branched, or cyclic. When Alk is cyclic, the alkyl group may consist of three to six carbon atoms (i.e., C$_{3-6}$ cycloalkyl). The alkyl group may be saturated or unsaturated with one or more carbon-carbon double bonds and/or carbon-carbon triple bonds.

When R$_8$ is

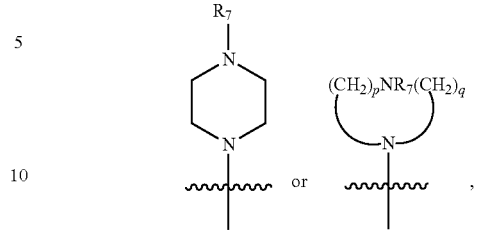

R$_7$ is H or alkyl. When R$_7$ is alkyl, the alkyl group can be an aliphatic carbon group consisting of 1 to 6 carbon atoms (i.e., C$_{1-6}$ alkyl). The alkyl group may be linear, branched, or cyclic. When the alkyl group is cyclic, the alkyl group may consist of three to six carbon atoms (i.e., C$_{3-6}$ cycloalkyl). The alkyl group may be saturated or unsaturated with one or more carbon-carbon double bonds and/or carbon-carbon triple bonds. In some embodiments, R$_7$ is H. In other embodiments, R$_7$ is methyl. In other embodiments, R$_7$ is ethyl. In other embodiments, R$_7$ is propyl (e.g., n-propyl or isopropyl). In other embodiments, R$_7$ is butyl (e.g., 1-butyl, 2-butyl, or t-butyl). In other embodiments, R$_7$ is pentyl (e.g., 1-n-pentyl, 2-n-pentyl, 3-n-pentyl, 2-methylbut-4-yl, 2-methylbutyl-3-yl, or 1-dimethylprop-1-yl). In other embodiments, R$_7$ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethylbut-4-yl, 2,2-dimethylbut-4-yl, 3,3-dimethylbut-4-yl, 2,3,3-trimethylprop-3-yl, 1,1-dimethylbut-1-yl, or 1,2,2-trimethylbut-1-yl).

When R$_8$ is

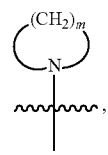

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

When R$_8$ is

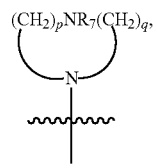

p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3.

EDG is one or more amino, aryl, acylamido, acyloxy, alkoxy or alkyl electron donating groups. EDG may be a single electron donating substituent in the ortho-, meta-, or para-position of the aryl ring. In some embodiments, the single EDG substituent is at the ortho-position of the aryl ring. In other embodiments, the single EDG substituent is at the para-position of the aryl ring. In other embodiments, EDG may be two to five electron donating groups in any combination of ortho-, meta-, and para-positions of the aryl ring. In some embodiments, two EDG substituents are at the two ortho-positions of the aryl ring. In other embodiments, one EDG substituent is at the ortho-position and a second same or different EDG substituent is at the para-position of the aryl ring. In other embodiments, one EDG substituent is at one ortho-position of the aryl ring and a second same or different EDG substituent is at the other ortho-position of the aryl ring. In some embodiments, one EDG substituent is at one ortho-position of the aryl ring, a second same or different EDG substituent is at the other ortho-position of the aryl ring, and a third same or different EDG substituent is at the para-position of the aryl ring.

Each EDG may be independently selected from amino, aryl, acylamido, acyloxy, alkoxy or alkyl. When EDG is amino, the amino group may be —$NH_2$, —N(H)Alk, or —$N(Alk)_2$, with each Alk being an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is aryl, the aryl substituent may be substituted or unsubstituted. The aryl substituent may be heteroatomic, such as a pyridine ring, a pyrazine ring, or a triazine ring that is substituted or unsubstituted. When EDG is acylamido, the acylamido group has a general formula of —$N(H)COR_9$, with $R_9$ being substituted or unsubstituted alkyl. When EDG is acyloxy, the acyloxy group has a general formula of —$OC(O)R_9$, with $R_9$ being substituted or unsubstituted alkyl. When EDG is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds. In some embodiments, EDG is para-alkoxy, such as para-methoxy, para-ethoxy, or para-propoxy.

Some example compounds of formula (IV) are provided in Table 4 below.

TABLE 4

Example Compounds of Formula (IV)

| Compound | $R_1$ | $R_8$ | Alk | EDG | $R_7$ | m | n | p | q |
|---|---|---|---|---|---|---|---|---|---|
| 2290 | H | —$N(Alk)_2$ | Me | p-OMe | n/a | n/a | 2 | n/a | n/a |
| 2291 | m-Cl | —$N(Alk)_2$ | Me | p-OMe | n/a | n/a | 2 | n/a | n/a |
| 2292 | m-Cl p-Cl | —$N(Alk)_2$ | Me | p-OMe | n/a | n/a | 2 | n/a | n/a |
| 2293 | o-OMe | —$N(Alk)_2$ | Me | p-OMe | n/a | n/a | 2 | n/a | n/a |
| 2294 | p-OMe | —$N(Alk)_2$ | Me | p-OMe | n/a | n/a | 2 | n/a | n/a |
| 2295 | o-Me | —$N(Alk)_2$ | Me | p-OMe | n/a | n/a | 2 | n/a | n/a |

TABLE 4-continued

Example Compounds of Formula (IV)

| Compound | $R_1$ | $R_8$ | Alk | EDG | $R_7$ | m | n | p | q |
|---|---|---|---|---|---|---|---|---|---|
| 2296 | m-$OCF_3$ | —$N(Alk)_2$ | Me | p-OMe | n/a | n/a | 2 | n/a | n/a |
| 2297 | m-$CF_3$ p-Cl | —$N(Alk)_2$ | Me | p-OMe | n/a | n/a | 2 | n/a | n/a |
| 2298 | 2-Cl 5-Cl | —$N(Alk)_2$ | Me | p-OMe | n/a | n/a | 2 | n/a | n/a |
| 2299 | m-Cl p-F | —$N(Alk)_2$ | Me | p-OMe | n/a | n/a | 2 | n/a | n/a |
| 2300 | 2-F 3-Cl | —$N(Alk)_2$ | Me | p-OMe | n/a | n/a | 2 | n/a | n/a |
| 2301 | o-$CF_3$ | —$N(Alk)_2$ | Me | p-OMe | n/a | n/a | 2 | n/a | n/a |
| 2302 | H | —$NH_2$ | Me | p-OMe | n/a | n/a | 2 | n/a | n/a |
| 2303 | H | 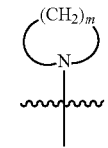 | Me | p-OMe | n/a | 5 | 2 | n/a | n/a |
| 2304 | H | 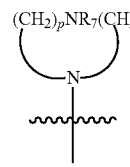 | Me | p-OMe | Me | n/a | 2 | 2 | 2 |

Figure 4:
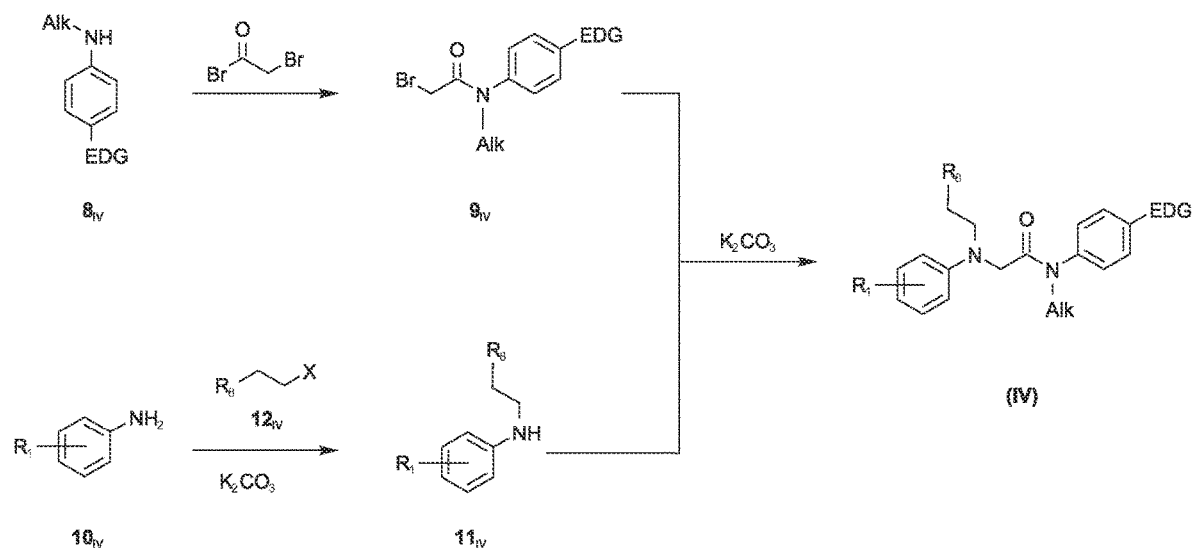
FIG. 4 shows a representative synthetic route for producing compounds of formula (IV).

Referring now to FIG. 4, compounds consistent with formula (IV) can be synthesized by, for example, acylating alkylanilines $8_{IV}$ with bromoacetyl bromide to form α-bromoamido intermediates $9_{IV}$. Intermediates $111_{IV}$ can be formed by alkylating anilines $10_{IV}$ with β-haloamines $12_{IV}$ in the presence of base. Combining intermediates $11_{IV}$ with the α-bromoamido intermediates $9_{IV}$ in the presence of base yields compounds of formula (IV).

The present disclosure provides compounds of formula (V):

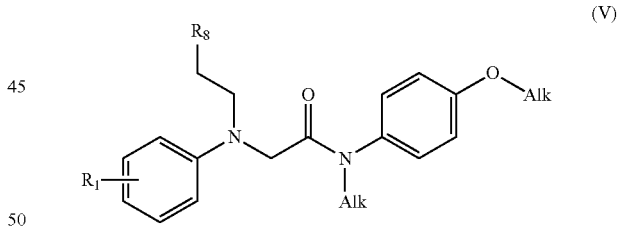

(V)

wherein:
$R_1$ is H, Cl, F, —$CF_3$, —$OCF_3$, or —OMe;
$R_8$ is selected from the group consisting of:
—$NH_2$, —N(H)Alk, —$N(Alk)_2$,

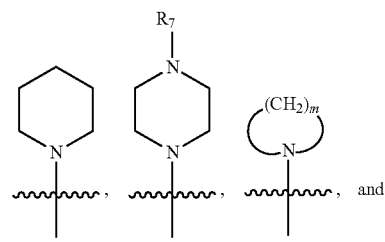

, , , and

-continued

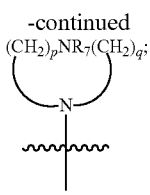

R₇ is H or alkyl;
m is 3 to 6;
p is 1 to 4;
q is 1 to 4;
p+q is 3 to 6; and
each Alk is independently an aliphatic carbon group consisting of 1 to 6 carbon atoms.

In compounds of formula (V), $R_1$ is H or one or more substituents each independently selected from the group consisting of: chloro, fluoro, trifluoromethyl, trifluoromethoxy, and methoxy. For example and without limitation, $R_1$ may in some embodiments be a single substituent that is chloro, fluoro, trifluoromethyl, trifluoromethoxy, or methoxy that is located at the ortho-, meta-, or para-position of the aryl ring. In other embodiments, $R_1$ is two or more substituents each independently selected from chloro, fluoro, trifluoromethyl, trifluoromethoxy, and methoxy located at any combination of the ortho-positions, the meta-positions, and the para-position of the aryl ring.

$R_8$ is an n-amino substituent selected from $-NH_2$, $-N(H)Alk$, $-N(Alk)_2$,

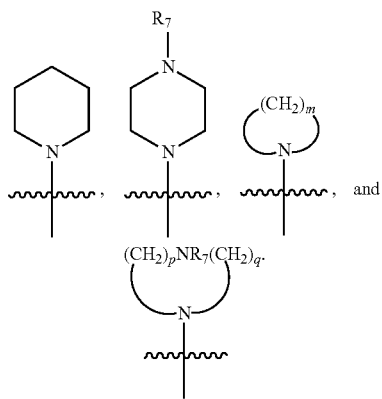

When $R_8$ is $-N(H)Alk$ or $-N(Alk)_2$, Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

When $R_8$ is

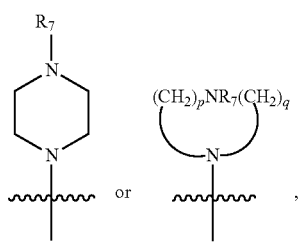

$R_7$ is H or alkyl. When $R_7$ is alkyl, the alkyl group can be an aliphatic carbon group consisting of 1 to 6 carbon atoms (i.e., $C_{1-6}$ alkyl). The alkyl group may be linear, branched, or cyclic. When the alkyl group is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. In some embodiments, $R_7$ is H. In other embodiments, $R_7$ is methyl. In other embodiments, $R_7$ is ethyl. In other embodiments, $R_7$ is propyl (e.g., n-propyl or isopropyl). In other embodiments, $R_7$ is butyl (e.g., 1-butyl, 2-butyl, or t-butyl). In other embodiments, $R_7$ is pentyl (e.g., 1-n-pentyl, 2-n-pentyl, 3-n-pentyl, 2-methylbut-4-yl, 2-methylbutyl-3-yl, or 1-dimethylprop-1-yl). In other embodiments, $R_7$ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethylbut-4-yl, 2,2-dimethylbut-4-yl, 3,3-dimethylbut-4-yl, 2,3,3-trimethylprop-3-yl, 1,1-dimethylbut-1-yl, or 1,2,2-trimethylbut-1-yl).

When $R_8$ is

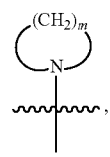

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

When $R_8$ is

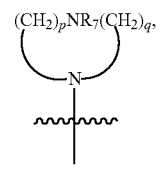

p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3.

Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

Some example compounds of formula (V) are provided in Table 5 below.

TABLE 5

| Example Compounds of Formula (V) | | | | | | | | |
|---|---|---|---|---|---|---|---|---|
| Compound | $R_1$ | $R_8$ | Alk | $R_7$ | m | n | p | q |
| 2290 | H | $-N(Alk)_2$ | Me | n/a | n/a | 2 | n/a | n/a |
| 2291 | m-Cl | $-N(Alk)_2$ | Me | n/a | n/a | 2 | n/a | n/a |

TABLE 5-continued

Example Compounds of Formula (V)

| Compound | R₁ | R₈ | Alk | R₇ | m | n | p | q |
|---|---|---|---|---|---|---|---|---|
| 2292 | m-Cl, p-Cl | —N(Alk)₂ | Me | n/a | n/a | 2 | n/a | n/a |
| 2293 | o-OMe | —N(Alk)₂ | Me | n/a | n/a | 2 | n/a | n/a |
| 2294 | p-OMe | —N(Alk)₂ | Me | n/a | n/a | 2 | n/a | n/a |
| 2295 | o-Me | —N(Alk)₂ | Me | n/a | n/a | 2 | n/a | n/a |
| 2296 | m-OCF₃ | —N(Alk)₂ | Me | n/a | n/a | 2 | n/a | n/a |
| 2297 | m-CF₃, p-Cl | —N(Alk)₂ | Me | n/a | n/a | 2 | n/a | n/a |
| 2298 | 2-Cl, 5-Cl | —N(Alk)₂ | Me | n/a | n/a | 2 | n/a | n/a |
| 2299 | m-Cl, p-F | —N(Alk)₂ | Me | n/a | n/a | 2 | n/a | n/a |
| 2300 | 2-F, 3-Cl | —N(Alk)₂ | Me | n/a | n/a | 2 | n/a | n/a |
| 2301 | o-CF₃ | —N(Alk)₂ | Me | n/a | n/a | 2 | n/a | n/a |
| 2302 | H | —NH₂ | Me | n/a | n/a | 2 | n/a | n/a |
| 2303 | H | 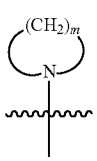 | Me | n/a | 5 | 2 | n/a | n/a |
| 2304 | H | 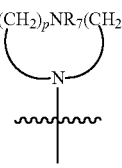 | Me | Me | n/a | 2 | 2 | 2 |

Figure 5:
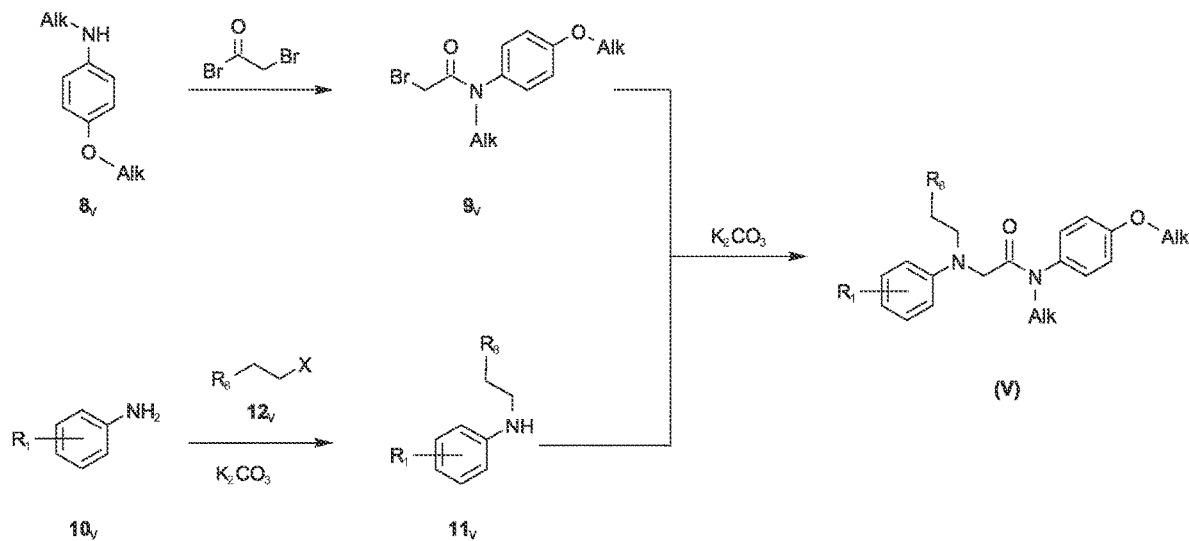
FIG. 5 shows a representative synthetic route for producing compounds of formula (V).

Referring now to FIG. 5, compounds consistent with formula (V) can be synthesized by, for example, acylating alkylaminoalkylphenols $8_V$ with bromoacetyl bromide to form α-bromoamido intermediates $9_V$. Intermediates $11_V$ can be formed by alkylating anilines $10_V$ with β-haloamines $12_V$ in the presence of base. Combining intermediates $11_V$ with α-bromoamido intermediates $9_V$ in the presence of base yields compounds of formula (V).

The present disclosure provides compounds of formula (VI):

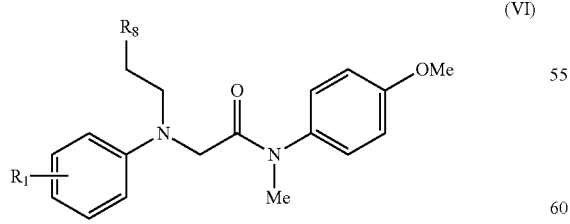

(VI)

wherein:

$R_1$ is H, Cl, F, —CF₃, —OCF₃, —OMe, or methyl;

$R_8$ is selected from the group consisting of:

—NH₂, —N(H)Alk, —N(Alk)₂,

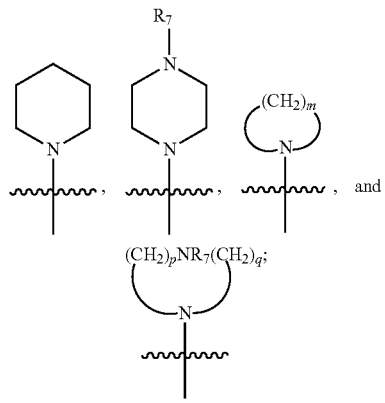

$R_7$ is H or alkyl;

m is 3 to 6;

p is 1 to 4;

q is 1 to 4;

p+g is 3 to 6; and each Alk is independently an aliphatic carbon group consisting of 1 to 6 carbon atoms.

In compounds of formula (VI), $R_1$ is H or one or more substituents each independently selected from the group consisting of: chloro, fluoro, trifluoromethyl, trifluoromethoxy, methoxy, and methyl. For example and without limitation, $R_1$ may in some embodiments be a single substituent that is chloro, fluoro, trifluoromethyl, trifluoromethoxy, or methoxy that is located at the ortho-, meta-, or para-position of the aryl ring. In other embodiments, $R_1$ is two or more substituents each independently selected from chloro, fluoro, trifluoromethyl, trifluoromethoxy, and methoxy located at any combination of the ortho-positions, the meta-positions, and the para-position of the aryl ring.

$R_8$ is an n-amino substituent selected from —NH₂, —N(H)Alk, —N(Alk)₂,

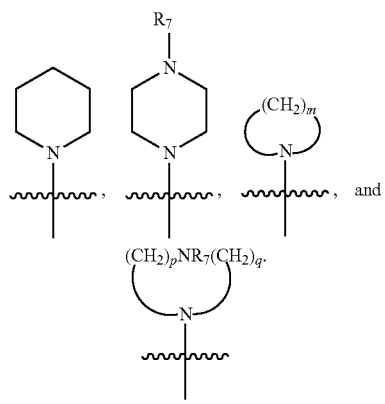

When $R_8$ is —N(H)Alk or —N(Alk)₂, Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

When R₈ is

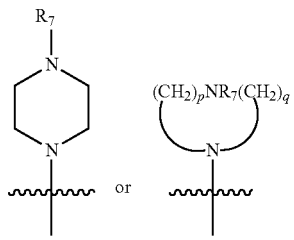

R₇ is H or alkyl. When R₇ is alkyl, the alkyl group can be an aliphatic carbon group consisting of 1 to 6 carbon atoms (i.e., $C_{1-6}$ alkyl). The alkyl group may be linear, branched, or cyclic. When the alkyl group is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. In some embodiments, R₇ is H. In other embodiments, R₇ is methyl. In other embodiments, R₇ is ethyl. In other embodiments, R₇ is propyl (e.g., n-propyl or isopropyl). In other embodiments, R₇ is butyl (e.g., 1-butyl, 2-butyl, or t-butyl). In other embodiments, R₇ is pentyl (e.g., 1-n-pentyl, 2-n-pentyl, 3-n-pentyl, 2-methylbut-4-yl, 2-methylbutyl-3-yl, or 1-dimethylprop-1-yl). In other embodiments, R₇ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethylbut-4-yl, 2,2-dimethylbut-4-yl, 3,3-dimethylbut-4-yl, 2,3,3-trimethylprop-3-yl, 1,1-dimethylbut-1-yl, or 1,2,2-trimethylbut-1-yl).

When R₈ is

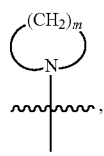

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

When R₈ is

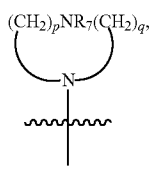

p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3. Some example compounds of formula (VI) are provided in Table 6 below.

TABLE 6

Example Compounds of Formula (VI)

| Compound | R₁ | R₈ | Alk | R₇ | m | n | p | q |
|---|---|---|---|---|---|---|---|---|
| 2290 | H | —N(Alk)₂ | Me | n/a | n/a | 2 | n/a | n/a |
| 2291 | m-Cl | —N(Alk)₂ | Me | n/a | n/a | 2 | n/a | n/a |
| 2292 | m-Cl p-Cl | —N(Alk)₂ | Me | n/a | n/a | 2 | n/a | n/a |
| 2293 | o-OMe | —N(Alk)₂ | Me | n/a | n/a | 2 | n/a | n/a |
| 2294 | p-OMe | —N(Alk)₂ | Me | n/a | n/a | 2 | n/a | n/a |
| 2295 | o-Me | —N(Alk)₂ | Me | n/a | n/a | 2 | n/a | n/a |
| 2296 | m-OCF₃ | —N(Alk)₂ | Me | n/a | n/a | 2 | n/a | n/a |
| 2297 | m-CF₃ p-Cl | —N(Alk)₂ | Me | n/a | n/a | 2 | n/a | n/a |
| 2298 | 2-Cl 5-Cl | —N(Alk)₂ | Me | n/a | n/a | 2 | n/a | n/a |
| 2299 | m-Cl p-F | —N(Alk)₂ | Me | n/a | n/a | 2 | n/a | n/a |
| 2300 | 2-F 3-Cl | —N(Alk)₂ | Me | n/a | n/a | 2 | n/a | n/a |
| 2301 | o-CF₃ | —N(Alk)₂ | Me | n/a | n/a | 2 | n/a | n/a |
| 2302 | H | —NH₂ | n/a | n/a | n/a | 2 | n/a | n/a |
| 2303 | H | (CH₂)ₘ ring with N | Me | n/a | 5 | 2 | n/a | n/a |
| 2304 | H | (CH₂)ₚNR₇(CH₂)_q ring with N | Me | Me | n/a | 2 | 2 | 2 |

Figure 6:
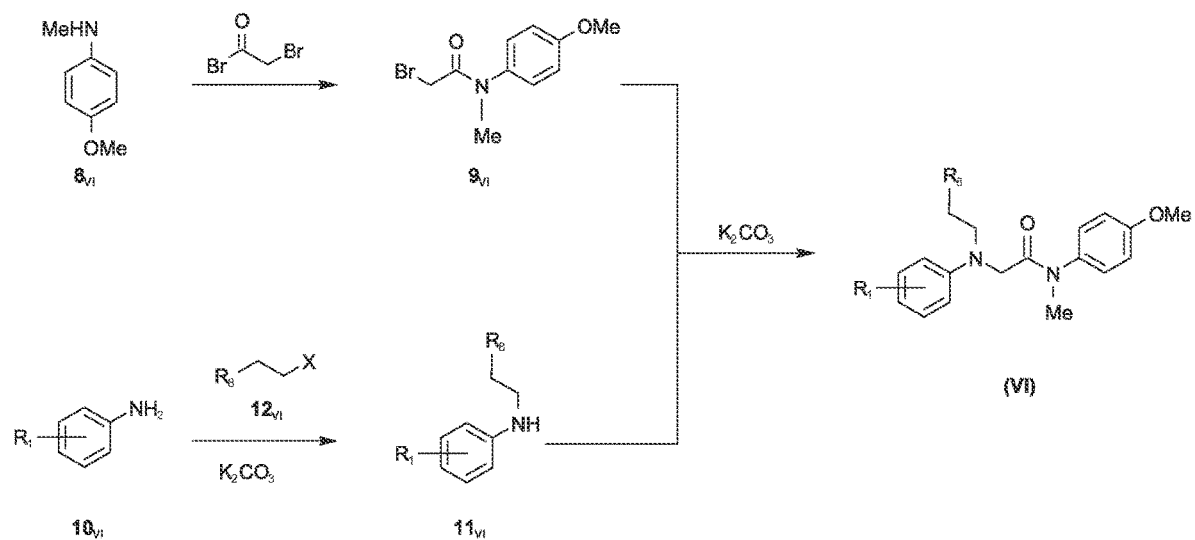
FIG. 6 shows a representative synthetic route for producing compounds of formula (VI).

Referring now to FIG. 6, compounds consistent with formula (VI) can be synthesized by, for example, acylating methylanilines $8_{VI}$ with bromoacetyl bromide to form intermediates $9_{VI}$. Intermediates $11_{VI}$ can be formed by alkylating anilines $10_{VI}$ with 3-haloamines $12_{VI}$ in the presence of base. Combining intermediates $11_{VI}$ with intermediates $9_{VI}$ in the presence of base yields compounds of formula (VI).

The present disclosure provides compounds of formula (VII):

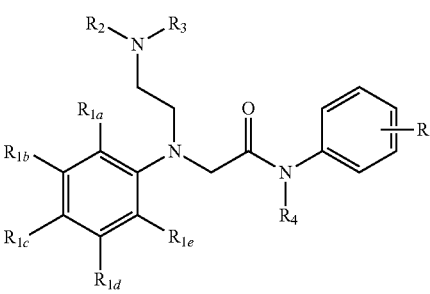

wherein:
  $R_{1a}$ is H, Cl, F, —CF₃, —OMe, or methyl;
  $R_{1b}$ is H, Cl, F, —CF₃, or —OCF₃;
  $R_{1c}$ is H, Cl, F, or —OMe;
  $R_{1d}$ is H, Cl, F, —CF₃, or —OCF₃;
  $R_{1e}$ is H, Cl, F, —CF₃, —OMe, or methyl;
  R₂ and R₃ are each independently H or alkyl or, taken together, form a 4- to 8-membered heterocyclic ring with the adjacent nitrogen atom;

$R_4$ is H or alkyl; and $R_5$ is H or one or more electron donating groups.

In compounds of formula (VII), $R_{1a}$ is H or an ortho-substituent selected from the group consisting of: chloro, fluoro, trifluoromethyl, methoxy, or methyl. $R_{1b}$ is H or a meta-substituent selected from the group consisting of: chloro, fluoro, trifluoromethyl, or trifluoromethoxy. $R_{1c}$ is H a para-substituent selected from the group consisting of: chloro, fluoro, or methoxy. $R_{1d}$ is H or (e.g., when $R_{1b}$ is not H) a meta-substituent selected from the group consisting of: chloro, fluoro, trifluoromethyl, or trifluoromethoxy. $R_{1e}$ is H or (e.g., when $R_{1a}$ is not H) an ortho-substituent selected from the group consisting of: chloro, fluoro, trifluoromethyl, methoxy, or methyl. In some embodiments, $R_{1a}$ is chloro, $R_{1d}$ is chloro, and $R_{1b}$, $R_{1c}$, and $R_{1e}$ are each H. In other embodiments, $R_{1a}$ is fluoro, $R_{1b}$ is chloro, and $R_{1c}$, $R_{1d}$, and $R_{1e}$ are each H. In other embodiments, $R_{1a}$ is trifluoromethyl, and $R_{1b}$, $R_{1c}$, $R_{1d}$, and $R_{1e}$ are each H. In other embodiments, $R_{1a}$ is methoxy, and $R_{1b}$, $R_{1c}$, $R_{1d}$, and $R_{1e}$ are each H. In other embodiments, $R_{1a}$ is methyl, and $R_{1b}$, $R_{1c}$, $R_{1d}$, and $R_{1e}$ are each H. In other embodiments, $R_{1b}$ is chloro, $R_{1c}$ is fluoro, and $R_{1a}$, $R_{1d}$, and $R_{1e}$ are each H. In other embodiments, $R_{1b}$ is trifluoromethyl, $R_{1c}$ is chloro, and $R_{1a}$, $R_{1d}$, and $R_{1e}$ are each H. In other embodiments, $R_{1b}$ is trifluoromethoxyl, and $R_{1a}$, $R_{1c}$, $R_{1d}$, and $R_{1e}$ are each H. In other embodiments, $R_{1b}$ is chloro, $R_{1c}$ is chloro, and $R_{1a}$, $R_{1d}$, and $R_{1e}$ are each H. In other embodiments, $R_{1b}$ is chloro, and $R_{1a}$, $R_{1c}$, $R_{1d}$, and $R_{1e}$ are each H. In other embodiments, $R_{1c}$ is methoxyl, and $R_{1a}$, $R_{1b}$, $R_{1d}$, and $R_{1e}$ are each H.

Each $R_2$ and $R_3$ is independently H or alkyl. When $R_2$ and/or $R_3$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

In some embodiments, $R_2$ and $R_3$ are covalently connected to form, with the adjacent nitrogen atom, a heterocyclic ring. The heterocyclic ring may include one to three nitrogen atoms and a total of four to eight atoms in the ring. The heterocyclic ring may be unsubstituted or substituted, for example with an alkyl or alkoxyl group. For example and without limitation, $R_2$ and $R_3$ may be covalently connected and include a total of five carbon atoms to form a piperidinyl ring including the nitrogen atom adjacent to $R_2$ and $R_3$. In other embodiments, $R_2$ and $R_3$ may, together, have a general formula $-(CH_2)_pN(R_7)(CH_2)_q-$, wherein p is 1 to 4, q is 1 to 4, p and q combined total 3 to 8, and $R_7$ is H or alkyl. When $R_7$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. In some embodiments, $R_2$ and $R_3$ are both H. In other embodiments, $R_2$ and $R_3$ are both methyl. In still other embodiments, $R_2$ is H and $R_3$ is methyl.

$R_4$ is H or alkyl. When $R_4$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

$R_5$ is H or one or more electron donating groups. When $R_5$ is one or more electron donating groups, $R_5$ may be a single electron donating group in the ortho-, meta-, or para-position of the aryl ring. In other embodiments, $R_5$ may be two to five electron donating groups in any combination of ortho-, meta-, and para-positions of the aryl ring. Each electron donating group may be independently selected from alkyl and alkoxyl. When $R_5$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When $R_5$ is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds.

Some example compounds of formula (VII) are provided in Table 7 below.

TABLE 7

Example Compounds of Formula (VII)

| Compound | $R_{1x}$ | $R_2$ | $R_3$ | $R_4$ | $R_5$ | $R_7$ | n | p | q |
|---|---|---|---|---|---|---|---|---|---|
| 2290 | a-e: H | Me | Me | Me | p-OMe | n/a | 2 | n/a | n/a |
| 2291 | a: H<br>b: Cl<br>c-e: H | Me | Me | Me | p-OMe | n/a | 2 | n/a | n/a |
| 2292 | a: H<br>b: Cl<br>c: Cl<br>d-e: H | Me | Me | Me | p-OMe | n/a | 2 | n/a | n/a |
| 2293 | a: OMe<br>b-e: H | Me | Me | Me | p-OMe | n/a | 2 | n/a | n/a |
| 2294 | a-b: H<br>c: OMe<br>d-e: H | Me | Me | Me | p-OMe | n/a | 2 | n/a | n/a |
| 2295 | a: Me<br>b-e: H | Me | Me | Me | p-OMe | n/a | 2 | n/a | n/a |
| 2296 | a: H<br>b: OCF$_3$<br>c-e: H | Me | Me | Me | p-OMe | n/a | 2 | n/a | n/a |

TABLE 7-continued

Example Compounds of Formula (VII)

| Compound | $R_{1x}$ | $R_2$ | $R_3$ | $R_4$ | $R_5$ | $R_7$ | n | p | q |
|---|---|---|---|---|---|---|---|---|---|
| 2297 | a: H<br>b: $CF_3$<br>c: Cl<br>d-e: H | Me | Me | Me | p-OMe | n/a | 2 | n/a | n/a |
| 2298 | a: Cl<br>b-c: H<br>d: Cl<br>e: H | Me | Me | Me | p-OMe | n/a | 2 | n/a | n/a |
| 2299 | a: H<br>b: Cl<br>c: F<br>d-e: H | Me | Me | Me | p-OMe | n/a | 2 | n/a | n/a |
| 2300 | a: F<br>b: Cl<br>c-e: H | Me | Me | Me | p-OMe | n/a | 2 | n/a | n/a |
| 2301 | a: $CF_3$<br>b-e: H | Me | Me | Me | p-OMe | n/a | 2 | n/a | n/a |
| 2302 | a-e: H | H | H | Me | p-OMe | n/a | 2 | n/a | n/a |
| 2303 | a-e: H | —$(CH_2)_5$— | | Me | p-OMe | n/a | 2 | n/a | n/a |
| 2304 | a-e: H | —$(CH_2)_p N(R_7)(CH_2)_q$— | | Me | p-OMe | Me | 2 | 2 | 2 |

Figure 7:
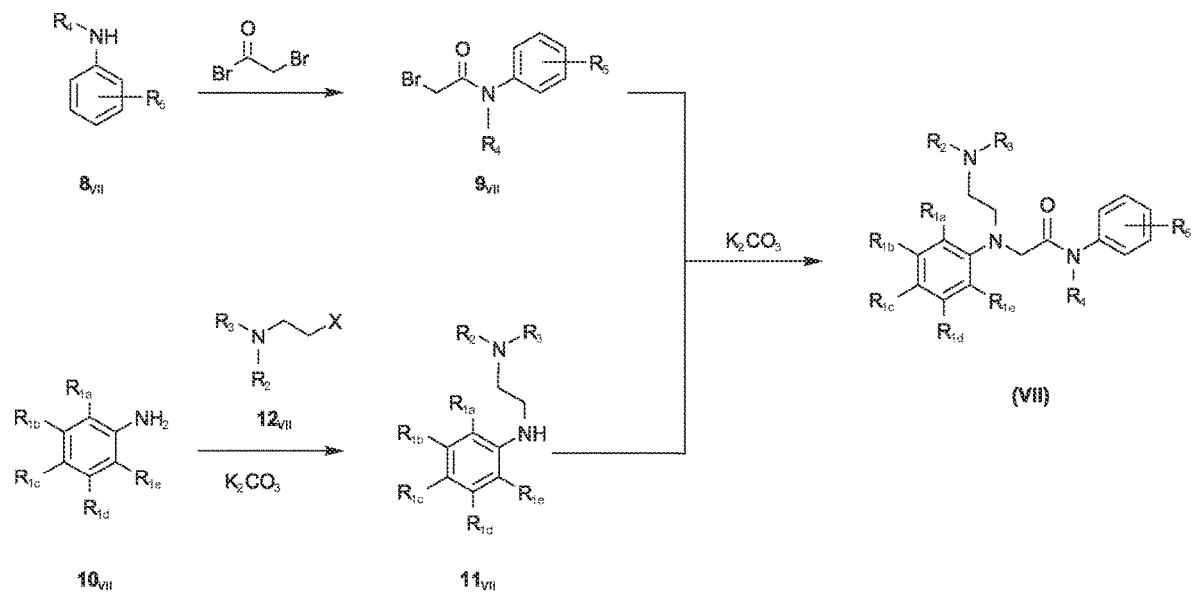
FIG. 7 shows a representative synthetic route for producing compounds of formula (VII).

Referring now to FIG. 7, compounds consistent with formula (VII) can be synthesized by, for example, acylating anilines $8_{VII}$ with bromoacetyl bromide to form intermediates $9_{VII}$. Intermediates $11_{VII}$ can be formed by alkylating anilines $10_{VII}$ with β-haloamines $12_{VII}$ in the presence of base. Combining intermediates $11_{VII}$ with intermediates $9_{VII}$ in the presence of base yields compounds of formula (VII).

2. Anesthetic Compositions

The present disclosure provides compositions comprising a compound of any one of formulas (I) to (VII). In some embodiments, the compound is present in an amount effective to treat perceived pain or to prevent expected pain in a subject after the composition is applied to skin of the subject proximal to the perceived pain or the expected pain. In some embodiments, the compound is present in an amount of about 0.01% w/w to about 5% w/w, in an amount of about 0.05% w/w to about 2% w/w, or in an amount of about 0.1% w/w to about 1% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w.

In some embodiments, the composition further comprises a carrier. In some embodiments, the carrier comprises, consists essentially of, or consists of water. In some embodiments, the carrier includes one or more solubilizing agents such as a hydrophobic solvent, an amphipathic solvent, a co-solvent, an emulsifier, a surfactant, etc.

In some embodiments, the composition further comprises a penetration enhancer, for example to enhance passage of the compound through skin of the subject. For example and without limitation, a composition of the present disclosure may include a vasodilator.

Compositions of the present disclosure may be in the form of a lotion, a cream, a gel, a stick, a spray, an ointment, or a paste. In some embodiments, the composition may be applied to skin of the subject using a dispenser. In other embodiments, the composition may be applied to skin of the subject using a dressing, a patch or a pad.

3. Methods of Treating or Preventing Pain

The present disclosure provides methods of treating or preventing pain in a subject. In some embodiments, the method comprises topically applying a composition of the present disclosure including a compound of any one of formulas (I) to (VII) to tissue (e.g., skin) of the subject. In some embodiments, the step of topically applying the composition occurs after the subject observes a pain sensation, and the composition is applied to tissue proximal to the observed pain sensation. In other embodiments, the step of topically applying the composition occurs before the subject observes a pain sensation, and the composition is applied to tissue proximal to a location where a pain sensation is expected to be observed by the subject.

EXAMPLES

Example 1. Patch Clamp Testing

An examination of the in vitro effects of the compounds consistent with the present disclosure on ion channels Nav1.5 (a sodium voltage-gated channel alpha subunit found predominantly in cardiac muscle cells) and Nav1.7 (a sodium voltage-gated channel alpha subunit normally expressed in high levels in nociceptive pain neurons at dorsal root ganglion (DRG) and trigeminal ganglion and in sympathetic ganglion neurons) was performed using adult epithelial (ovarian) tissue CHO cells of Chinese hamsters (C. griseus) transformed with adenovirus 5 DNA and transfected with human ion channel cDNAs (ATCC, Manassas, VA; ChanTest Corp., Cleveland, OH). Cells were cultured in Ham's F-12 medium supplemented with 10% fetal bovine serum, 100 U/mL penicillin G sodium, 100 μg/mL streptomycin sulfate, and 500 μg/mL G418 aminoglycoside antibiotic.

Each compound was analyzed at concentrations of 1000 μM, 300 μM, 100 μM, 30 μM, 10 μM, 3 μM, 1 μM, and 0.3 μM. Lidocaine was included as a positive control at concentrations of 3000 μM, 1000 μM, 300 μM, 100 μM, 30 μM, 10 μM, 3 μM, and 1 μM. All tested compound formulations contained 0.3% DMSO. Each concentration of each compound was loaded into a well of a 384-well polypropylene compound plate using an automated liquid handling system (Integra Assist Plus, Integra) and then placed in the plate well of SyncroPatch 384PE (SP384PE; Nanion Technologies, Livingston, NJ) immediately before application of the cells.

Observed $IC_{50}$ values of the channel current inhibition for each test article are provided in Table 8 (Nav1.5 ion channel inhibition) and Table 9 (Nav1.7 ion channel inhibition).

TABLE 8

Inhibition of Nav1.5 Ion Channel

| Compound | $IC_{50}$, μM | | |
|---|---|---|---|
| | TP1A | TP2A | TP25B |
| 2290 | >1000 | >1000 | >1000 |
| 2291 | 808.5 | 740.3 | 692.5 |
| 2292 | 207.7 | 215.7 | 193.1 |
| 2293 | >1000 | >1000 | >1000 |
| 2294 | >1000 | >1000 | >1000 |
| 2295 | >1000 | >1000 | >1000 |
| 2296 | 254.4 | 235.9 | 221.6 |
| 2297 | 95.1 | 91.2 | 72.7 |
| 2298 | 249.4 | 240.3 | 204.0 |
| 2299 | 515.2 | 449.0 | 504.5 |
| 2300 | 327.0 | 307.0 | 259.2 |
| 2301 | 265.3 | 242.5 | 154.0 |
| 2302 | 124.1 | 96.8 | 75.9 |
| 2303 | 16.6 | 13.5 | 9.5 |
| 2304 | >1000 | 880.4 | 670.2 |
| Lidocaine (pos. control) | 453.2 | 15.8 | 68.7 |

TP1A = Tonic Block
TP2A = Inactivated State-Dependent Block
TP25B = Use-Dependent Block

TABLE 9

Inhibition of Nav1.7 Ion Channel

| Compound | $IC_{50}$, μM | | |
|---|---|---|---|
| | TP1A | TP2A | TP25B |
| 2290 | >1000 | >1000 | >1000 |
| 2291 | 561.4 | 463.1 | 490.4 |
| 2292 | 164.8 | 162.1 | 166.5 |
| 2293 | >1000 | >1000 | >1000 |
| 2294 | >1000 | >1000 | >1000 |
| 2295 | >1000 | >1000 | >1000 |
| 2296 | 265.4 | 231.2 | 210.5 |
| 2297 | 74.7 | 66.2 | 54.4 |
| 2298 | 272.5 | 228.6 | 220.5 |
| 2299 | 392.6 | 315.0 | 334.3 |
| 2300 | 546.4 | 672.8 | 625.8 |
| 2301 | 312.1 | 275.3 | 235.0 |
| 2302 | 70.2 | 77.9 | 55.4 |
| 2303 | 15.0 | 14.5 | 13.1 |
| 2304 | >1000 | >1000 | >1000 |

TABLE 9-continued

Inhibition of Nav1.7 Ion Channel

| Compound | $IC_{50}$, μM | | |
|---|---|---|---|
| | TP1A | TP2A | TP25B |
| Lidocaine (pos. control) | 407.8 | 23.7 | 112.7 |

TP1A = Tonic Block
TP2A = Inactivated State-Dependent Block
TP25B = Use-Dependent Block

What is claimed is:

1. A compound of formula (VI):

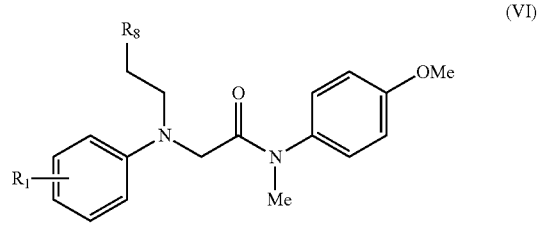

wherein:

$R_1$ is H, Cl, F, —$CF_3$, —$OCF_3$, —OMe, or methyl;

$R_8$ is selected from the group consisting of:

—$NH_2$, —N(H)Alk, —N(Alk)$_2$,

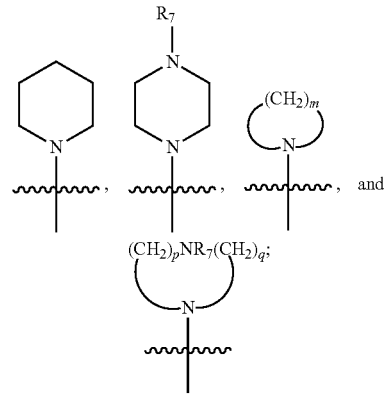

$R_7$ is H or alkyl;

m is 3 to 6;

p is 1 to 4;

q is 1 to 4;

p+q is 3 to 6; and each Alk is independently an aliphatic carbon group consisting of 1 to 6 carbon atoms.

2. The compound of claim 1, wherein:

$R_1$ is one or more of: H, meta-trifluoromethyl, meta-chloro, and para-chloro; and $R_8$ is —$NH_2$, N(H)Alk, N(Alk)$_2$,

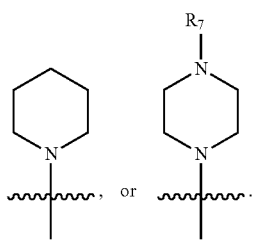

3. The compound of claim 1, wherein:
$R_1$ is methyl or methoxy; and
$R_8$ is —$NH_2$, $N(H)Alk$, $N(Alk)_2$,

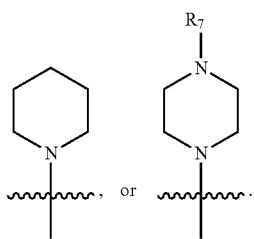

4. The compound of claim 1, wherein:
$R_1$ is methyl; and
$R_8$ is —$NH_2$, $N(H)Alk$, or $N(Alk)_2$.

5. The compound of claim 1, wherein:
$R_1$ is H, Cl, F, —$CF_3$, or —$OCF_3$; and
$R_8$ is —$NH_2$, $N(H)Alk$, or $N(Alk)_2$.

6. The compound of claim 1, wherein:
$R_1$ is Cl, F, —$CF_3$, or —$OCF_3$; and
$R_8$ is —$NH_2$, $N(H)Alk$, or $N(Alk)_2$.

7. The compound of claim 1, wherein:
$R_1$ is Cl, or F; and
$R_8$ is —$NH_2$, $N(H)Alk$, or $N(Alk)_2$.

8. The compound of claim 1 selected from the group consisting of:

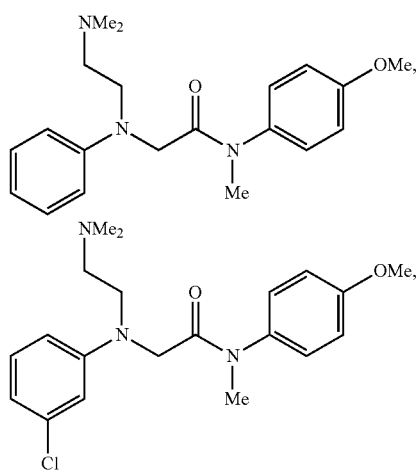

-continued

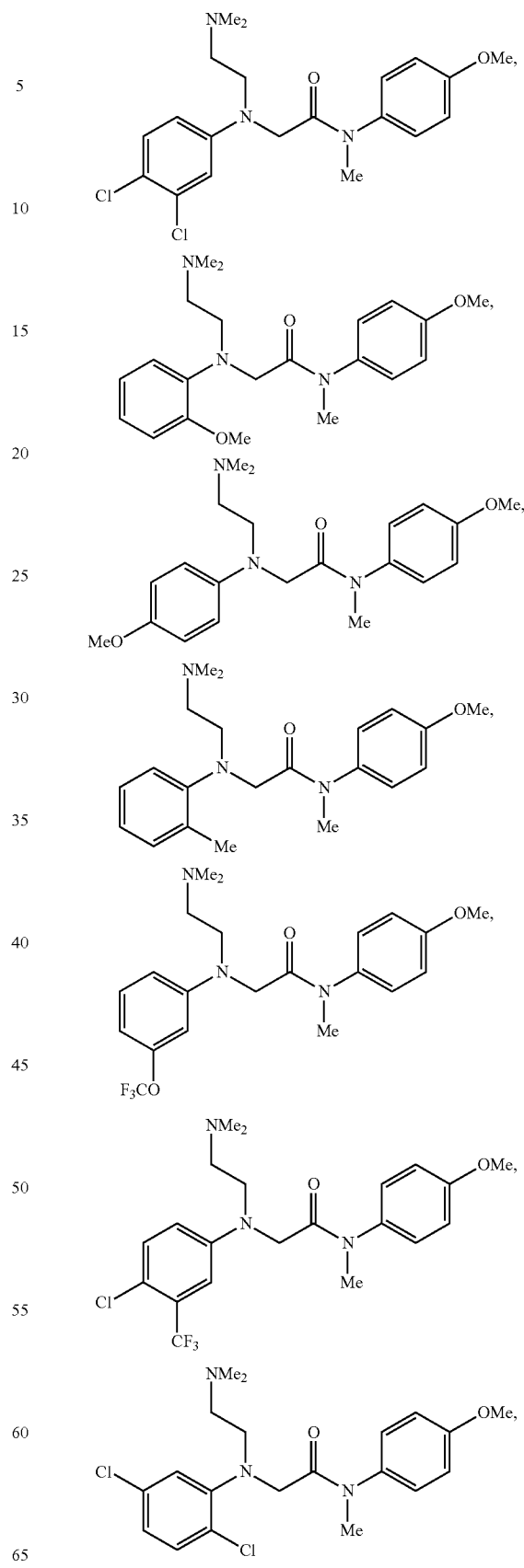

-continued
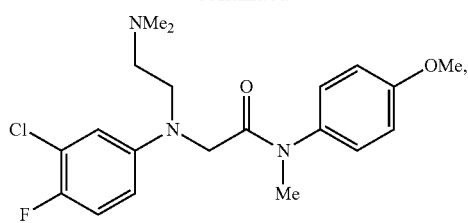
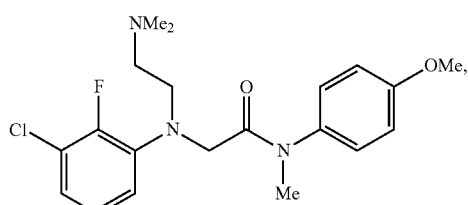
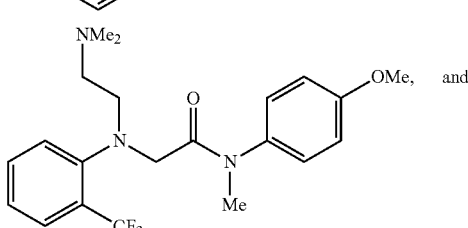
and
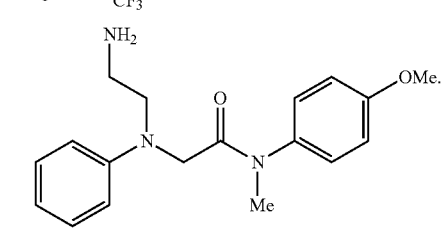
9. The compound of claim 1, wherein the compound is:
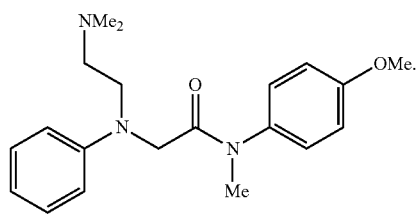 [SMILES: COc1ccc(N(C)C(=O)CN(CCN(C)C)c2ccccc2)cc1]
10. The compound of claim 1, wherein the compound is:
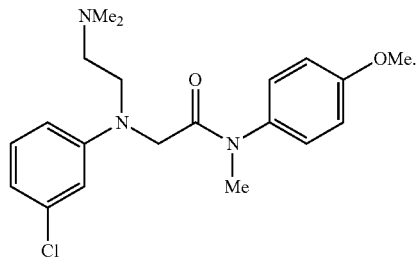 [SMILES: COc1ccc(N(C)C(=O)CN(CCN(C)C)c2cccc(Cl)c2)cc1]
11. The compound of claim 1, wherein the compound is:
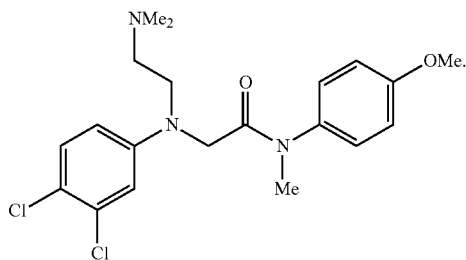 [SMILES: COc1ccc(N(C)C(=O)CN(CCN(C)C)c2ccc(Cl)c(Cl)c2)cc1]
12. The compound of claim 1, wherein the compound is:
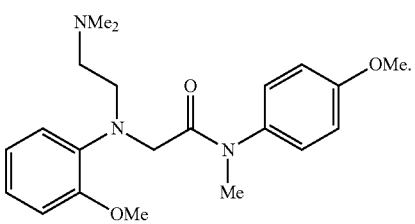 [SMILES: COc1ccc(N(C)C(=O)CN(CCN(C)C)c2ccccc2OC)cc1]
13. The compound of claim 1, wherein the compound is:
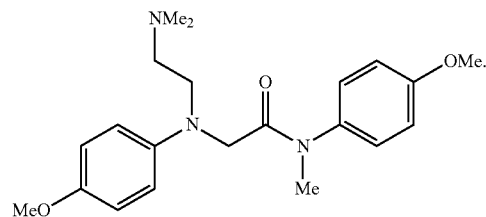 [SMILES: COc1ccc(N(CCN(C)C)CC(=O)N(C)c2ccc(OC)cc2)cc1]
14. The compound of claim 1, wherein the compound is:
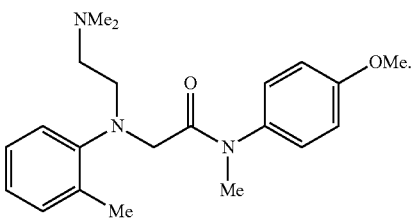 [SMILES: COc1ccc(N(C)C(=O)CN(CCN(C)C)c2ccccc2C)cc1]
15. The compound of claim 1, wherein the compound is:
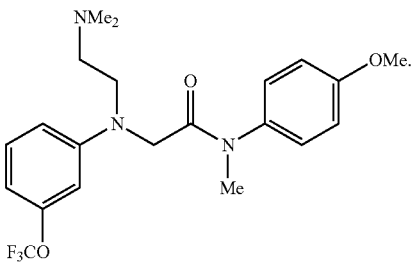 [SMILES: COc1ccc(N(C)C(=O)CN(CCN(C)C)c2cccc(OC(F)(F)F)c2)cc1]

16. The compound of claim 1, wherein the compound is:

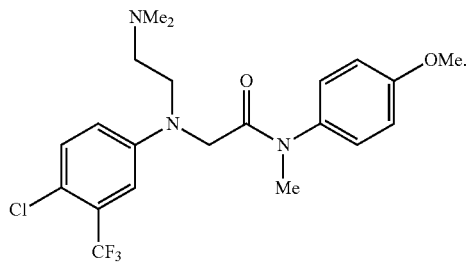

17. The compound of claim 1, wherein the compound is

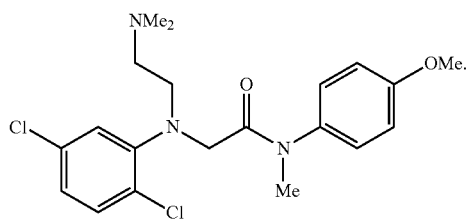 [SMILES: COc1ccc(N(C)C(=O)CN(CCN(C)C)c2cc(Cl)ccc2Cl)cc1]

18. The compound of claim 1, wherein the compound is

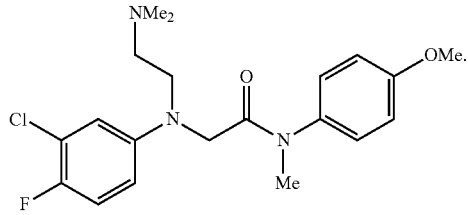 [SMILES: COc1ccc(N(C)C(=O)CN(CCN(C)C)c2ccc(F)c(Cl)c2)cc1]

19. The compound of claim 1, wherein the compound is

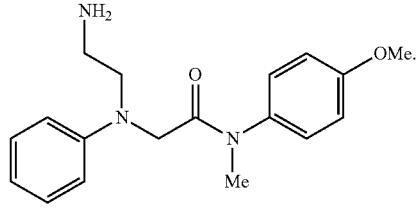 [SMILES: COc1ccc(N(C)C(=O)CN(CCN)c2ccccc2)cc1]

20. A method of treating or preventing pain in a subject in need thereof, the method comprising administering to the subject a compound selected from the group consisting of:

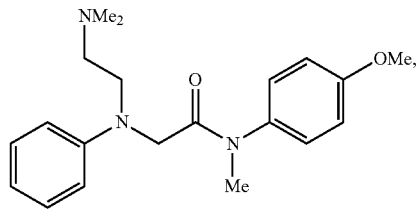

-continued

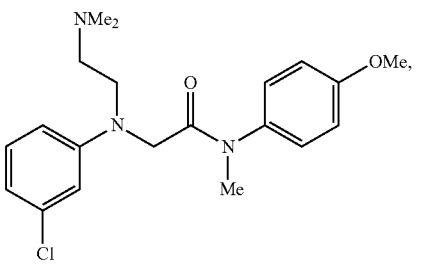

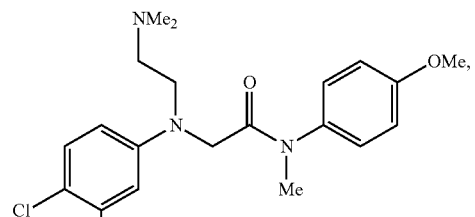

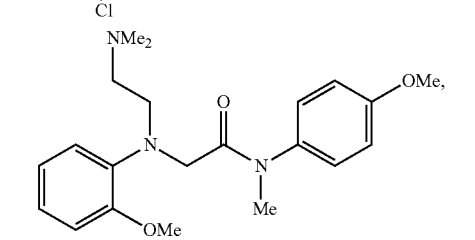

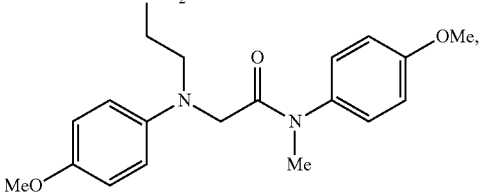

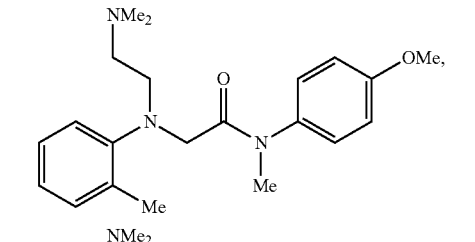

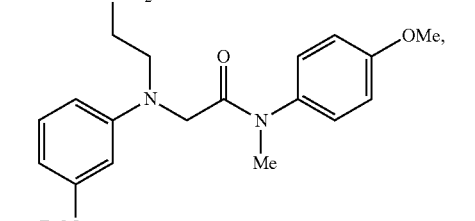

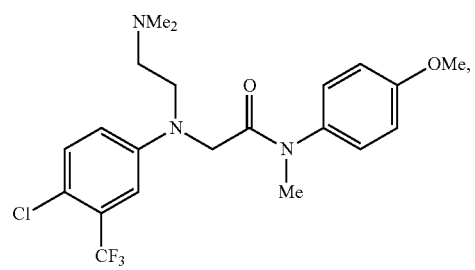

-continued
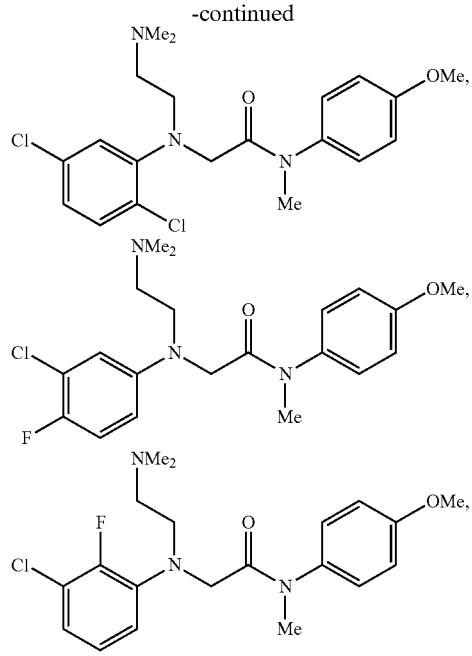
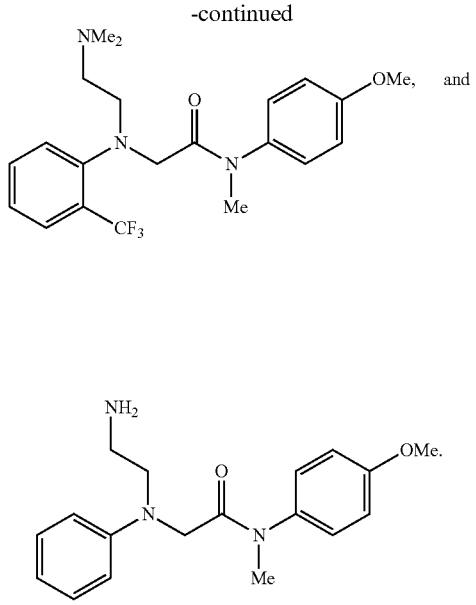
* * * * *